(12) United States Patent
Pourmand et al.

(10) Patent No.: US 7,223,540 B2
(45) Date of Patent: May 29, 2007

(54) TRANSIENT ELECTRICAL SIGNAL BASED METHODS AND DEVICES FOR CHARACTERIZING MOLECULAR INTERACTION AND/OR MOTION IN A SAMPLE

(75) Inventors: Nader Pourmand, San Carlos, CA (US); Arjang Hassibi, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 447 days.

(21) Appl. No.: 10/345,653

(22) Filed: Jan. 15, 2003

(65) Prior Publication Data

US 2003/0152985 A1    Aug. 14, 2003

Related U.S. Application Data

(62) Division of application No. 10/040,303, filed on Oct. 19, 2001.

(60) Provisional application No. 60/242,047, filed on Oct. 20, 2000, provisional application No. 60/285,578, filed on Apr. 20, 2001.

(51) Int. Cl.
    *C12Q 1/68* (2006.01)
(52) U.S. Cl. ........................................................ 435/6
(58) Field of Classification Search ................ None
    See application file for complete search history.

(56) References Cited

U.S. PATENT DOCUMENTS

| | | | |
|---|---|---|---|
| 4,863,849 A | 9/1989 | Melamede | |
| 5,405,746 A | 4/1995 | Uhlen | |
| 5,466,348 A | 11/1995 | Holm-Kennedy | |
| 5,565,322 A | 10/1996 | Heller | |
| 5,605,662 A | 2/1997 | Heller et al. | |
| 5,632,957 A | 5/1997 | Heller et al. | |
| 5,653,939 A | 8/1997 | Hollis et al. | |
| 5,674,743 A * | 10/1997 | Ulmer ............... | 435/287.2 |
| 5,871,918 A | 2/1999 | Thorp et al. | |
| 5,882,904 A | 3/1999 | Riedl et al. | |
| 5,958,701 A | 9/1999 | Green et al. | |
| 5,965,452 A | 10/1999 | Kovacs | |
| 5,968,745 A | 10/1999 | Thorp et al. | |
| 6,063,573 A | 5/2000 | Kayyem | |
| 6,071,699 A | 6/2000 | Meade et al. | |
| 6,087,100 A | 7/2000 | Meade et al. | |
| 6,090,933 A | 7/2000 | Kayyem et al. | |
| 6,096,273 A | 8/2000 | Kayyem et al. | |
| 6,100,045 A | 8/2000 | Van Es | |
| 6,120,676 A | 9/2000 | Heller et al. | |
| 6,127,127 A | 10/2000 | Eckhardt et al. | |
| 6,132,971 A | 10/2000 | Thorp et al. | |
| 6,180,346 B1 | 1/2001 | Thorp et al. | |
| 6,194,149 B1 | 2/2001 | Neri et al. | |
| 6,210,880 B1 | 4/2001 | Lyamichev et al. | |
| 6,225,059 B1 | 5/2001 | Ackley et al. | |
| 6,251,260 B1 | 6/2001 | Heller et al. | |
| 6,261,776 B1 | 7/2001 | Pirrung et al. | |
| 6,261,782 B1 | 7/2001 | Lizardi et al. | |
| 6,264,825 B1 | 7/2001 | Blackburn et al. | |
| 6,274,320 B1 | 8/2001 | Rothberg et al. | |
| 6,280,595 B1 | 8/2001 | Montgomery | |
| 6,281,006 B1 | 8/2001 | Heller et al. | |
| 6,287,776 B1 | 9/2001 | Hefti | |
| 6,287,874 B1 | 9/2001 | Hefti | |
| 6,322,963 B1 * | 11/2001 | Bauer ............................ | 435/4 |
| 6,518,024 B2 * | 2/2003 | Choong et al. ................ | 435/6 |
| 2002/0123048 A1 | 9/2002 | Gau | |

FOREIGN PATENT DOCUMENTS

| | | |
|---|---|---|
| WO | WO 99/14596 | 3/1999 |
| WO | WO 99/39001 | 5/1999 |
| WO | WO 99/67628 | 12/1999 |
| WO | WO 01/84145 | 8/2001 |

OTHER PUBLICATIONS

Kavanaugh et al (ANYL-61, ACS national meeting, 2004).*
Pourmand et al (PNAS (2006) 103:6466-6470).*
PCT Search Report, PCT/US01/51398, Jun. 7, 2002, pps. 1-3.
Armistead and Thorp, "Modification of Indium Tin Oxide Electrodes with Nucleic Acids: Detection of Attomole Quantities of Immobilized DNA by Electrocatalysis," *Anal. Chem.* 2000, 72, 3764-3770.
Bartic et al., "Organic-based transducer for low-cost charge detection in aqueous media," IEEE 2000.
Carter et al, "Effects of Secondary Structure on DNA and RNA Cleavage by Diplatinum (II)," *Biochemistry* 1998, 37, 13736-13743.
Edman et al. "Electric field directed nucleic acid hybridization on microchips," *Nucleic Acids Research*, 1997, vol. 25, No. 24, 4907-4914.

(Continued)

*Primary Examiner*—Jeffrey Fredman
(74) *Attorney, Agent, or Firm*—Peters Verny, LLP

(57) ABSTRACT

Devices for detecting a transient electrical signal in a sample are provided. Also provided are systems that include the subject devices. The subject devices and systems find use in a variety of applications, particularly in the characterization of a sample, and more particularly in the characterization of molecular entities in the sample.

16 Claims, 35 Drawing Sheets

OTHER PUBLICATIONS

Farrer and Thorp, "Redox Pathways in DNA Oxidation: Kinetic Studies of Guanine and Sugar Oxidation by Para-Substituted Derivatives of Oxoruthenium (IV)," *Inorg. Chem.* 2000, 39, 44-49.

Gupta et al.., "YBCO-FET room temperature ammonia sensor," *Sensors and Actuators*, B63:35-41 (2000).

Heller et al., "Active microelectronic chip devices which utilize controlled electrophoretic fields for multiplex DNA hybridization and other genomic applications," *Electrophoresis* 2000, 21, 157-164.

Huang et al., "Electric Manipulation of Bioparticles and Macromolecules on Microfabricated Electrodes," *Anal. Chem.* 2001, 73, 1549-1559.

Krider et al., "Automated Synthesis of 3'-Metalated Oligonucleotides," *Inorg. Chem.* 2001, 40, 4002-4009.

Lan et al., "Fingerprint Imager Based on a -Si:H Active-Matrix Photo-Diode Arrays," IEEE 2000.

Medoro et al., "CMOS-only sensors and manipulators for microorganisms," IEEE 2000.

Lumely-Woodyear et al, "Rapid Amperometric Verification of PCR Amplification of DNA," *Anal. Chem.* 1999, 71, 535-538.

Sosnowski et al, "Rapid determination of single base mismatch mutations in DNA hybrids by direct electric control," PNAS USA 94:1119-23, 1997.

Suing, Ethanol Oxidation by Imidorhenium (V) Complexes: Formation of Amidorhenium (III) Complexes, *Inorg. Chem.* 2000, 39, 6080-6085.

Takenaka et al, "DNA Sensing on a DNA Probe-Modified Electrode Using Ferrocenylnaphthalene Diimide as the Electrochemically Active Ligand," *Ana. Chem*, 2000, 72, 1334-1341.

Wang et al., "Polishable and Renewable DNA Hybridization Biosensors," *Anal. Chem.* 1998, 70m 3699-3702.

Weatherly et al., "Proton-Coupled Electron Transfer in Duplex DNA: Driving Force Dependence and Isotope Effects on Electrocatalytic Oxidation of Guanine," *J. Am. Chem. Soc.* 2001, 123, 1236-1237.

Yang and Thorp, "Kinetics of Metal-Mediated One-Electron Oxidation of Guanine in Polymeric DNA and in Oligonucleotides Containing Trinucleotide Repeat Sequences," *Inorg. Chem.* 2000, 39, 4969-4976.

Yang and Thorp, "Oxidation of 7-Deazaguanine by One-Electron and Oxo-Transfer Oxidants: Mismatch-Dependent Electrochemistry and Selective Strand Scission," *Inorg. Chem.* 2001, 40, 1690-1697.

John M. Shumaker, et al., "Mutation Detection by Solid Phase Primer Extension," *Human Mutation*, 1996, 7:346-354.

Koji Hshimoto, et al., "Sequence-Specific Gene Detection with a Gold Electrode Modified with DNA Probes and an Electrochemically Active Dye," *Analytical Chemistry*, Nov. 1, 1994, vol. 66, No. 21, 3830-3833.

Susan R. Mikkelsen, "Electrochemical Biosensors for DNA Sequence Detection," *Electroanalysis*, 1996, vol. 8, No. 1, 15-19.

Joseph Wang, et al., "Indicator-free electrochemical DNA hybridization biosensor," *Analytica Chimica Acta* 375, 1998, 197-203.

\* cited by examiner

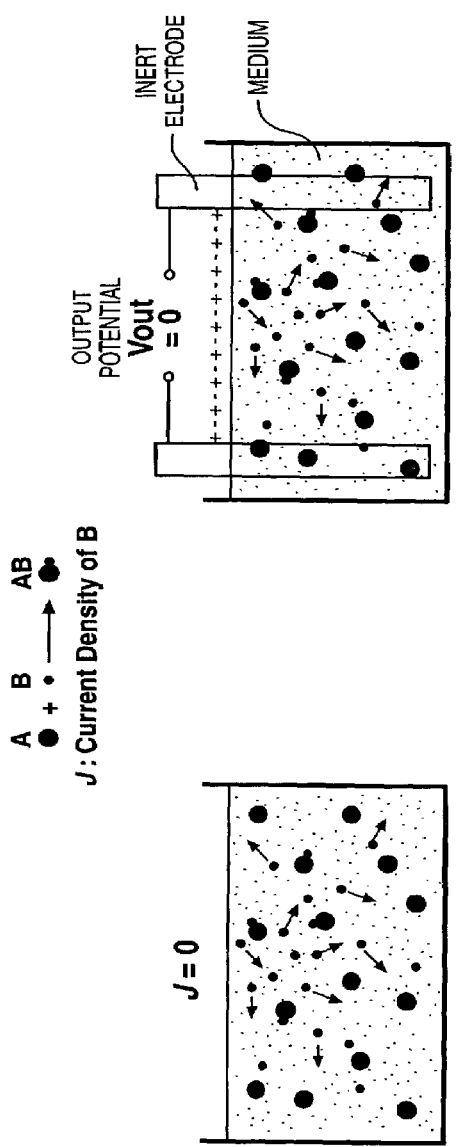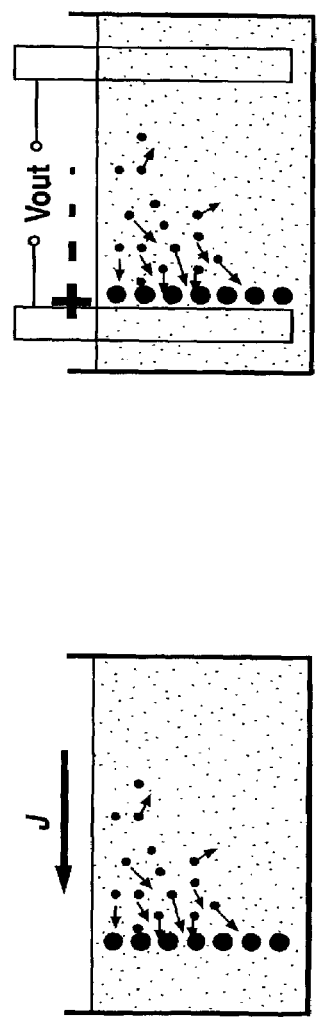
FIG. 1.1 1.1) If A and B are both free in the medium no net transient gradient of molecules (current density) is created.
FIG. 1.2 1.2) If A is spacially immobilized and B is free in the medium, the reaction causes a net transient gradient (current density) of B toward A. This transient current created a temporary potential difference in the medium.

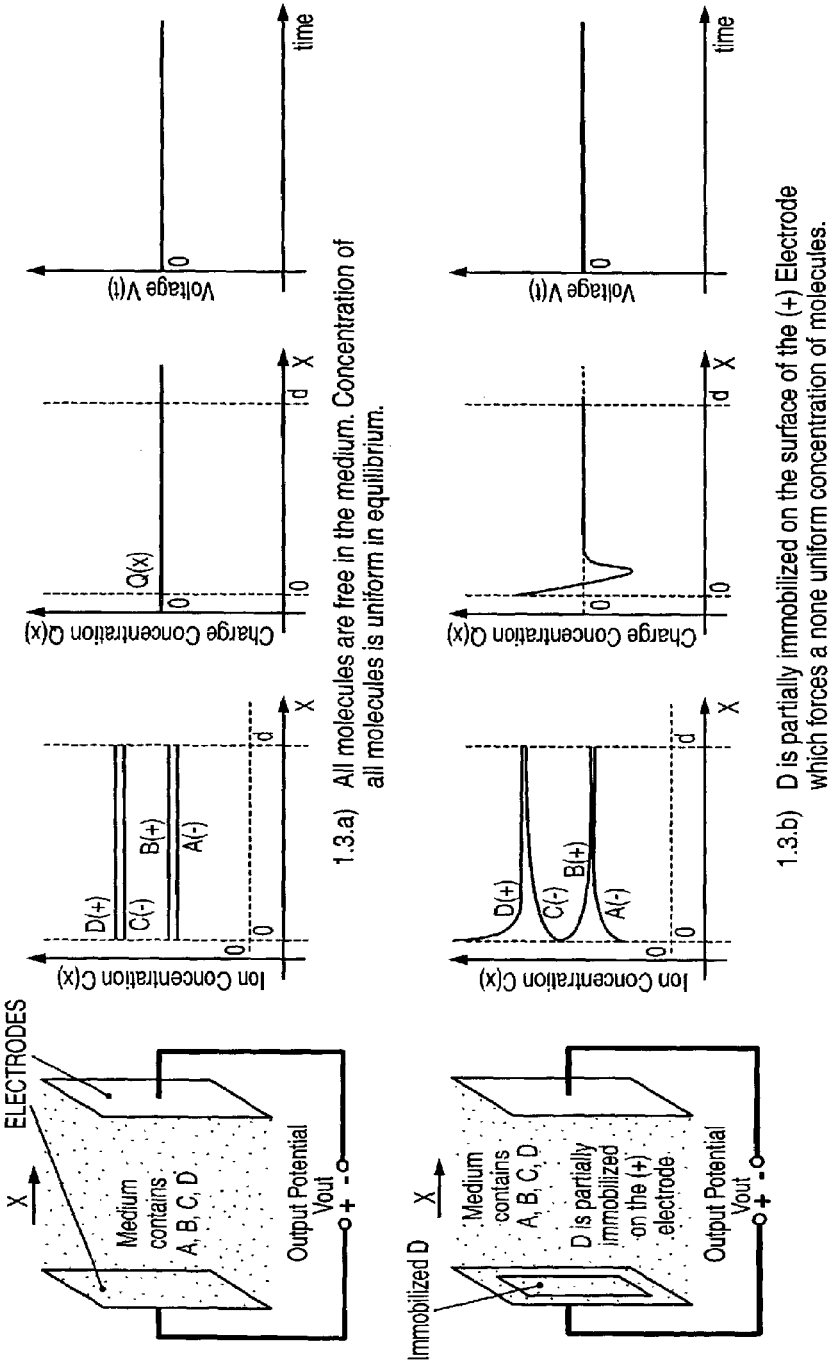

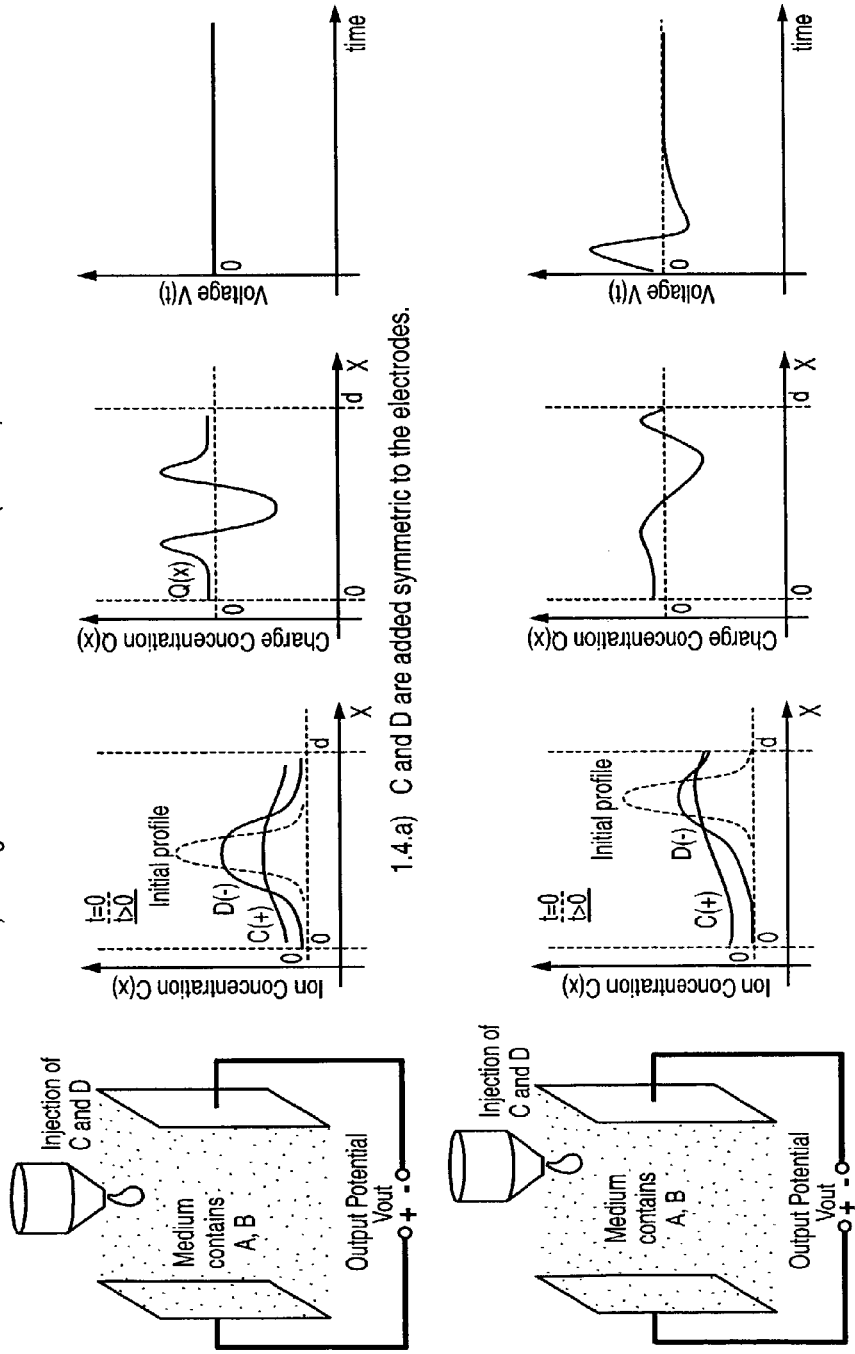

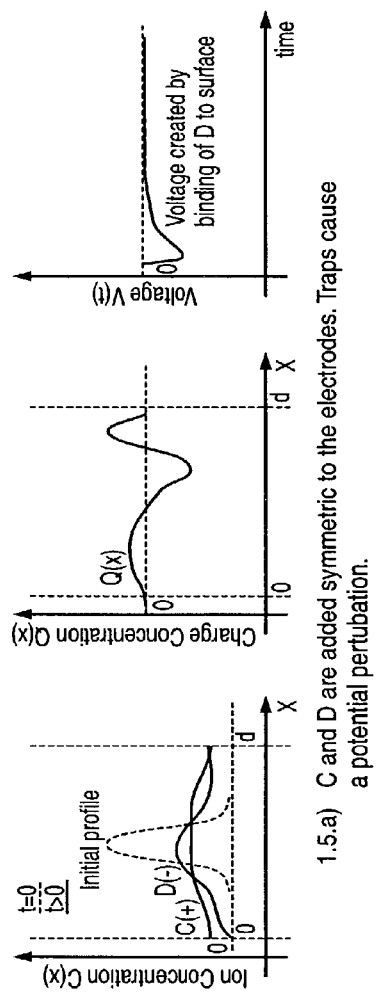
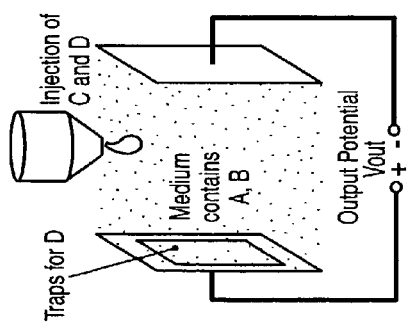
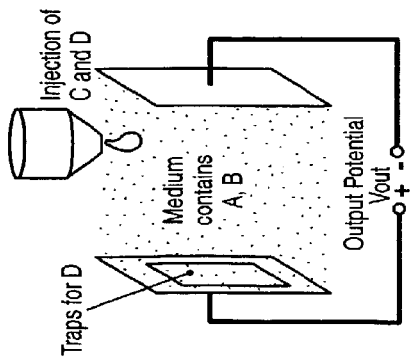

FIG. 2.1
Planar sensor design example:
1) Electrodes are inert and do not interact with the medium.
2) The target molecules are immobilized on the (+) electrode.
3) The (−) electrode is the reference electrode.
4) A differential amplifier subtracts the voltage from the two electrodes.
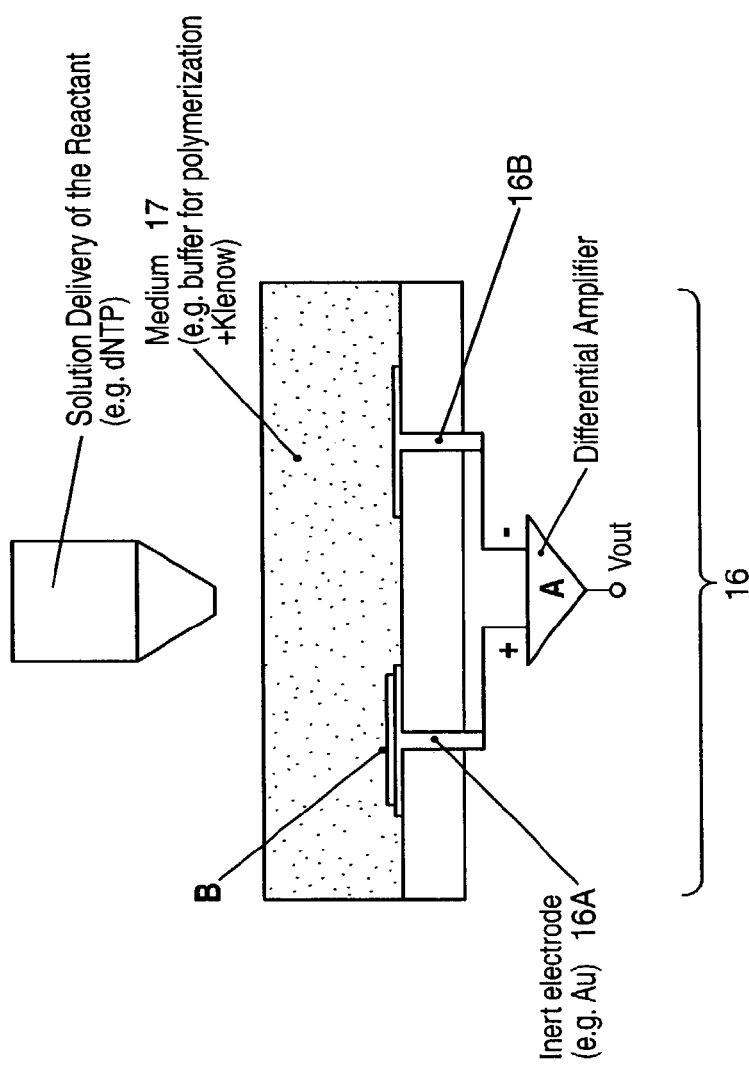

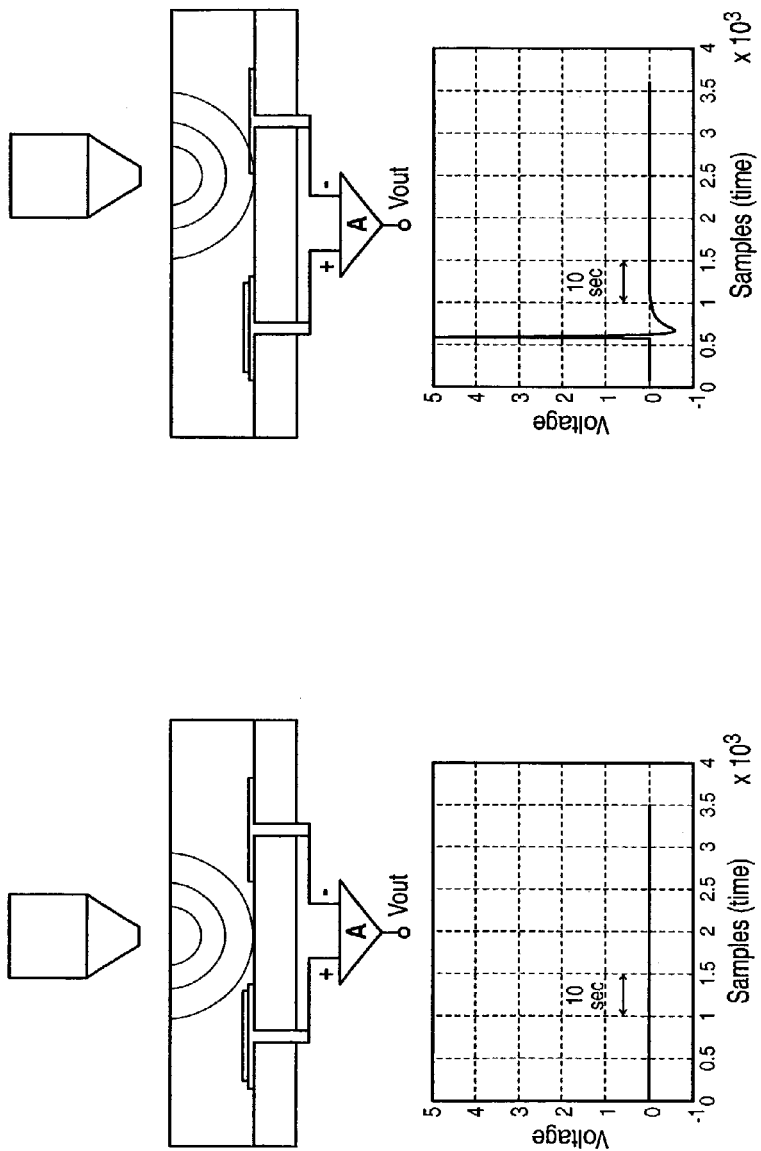

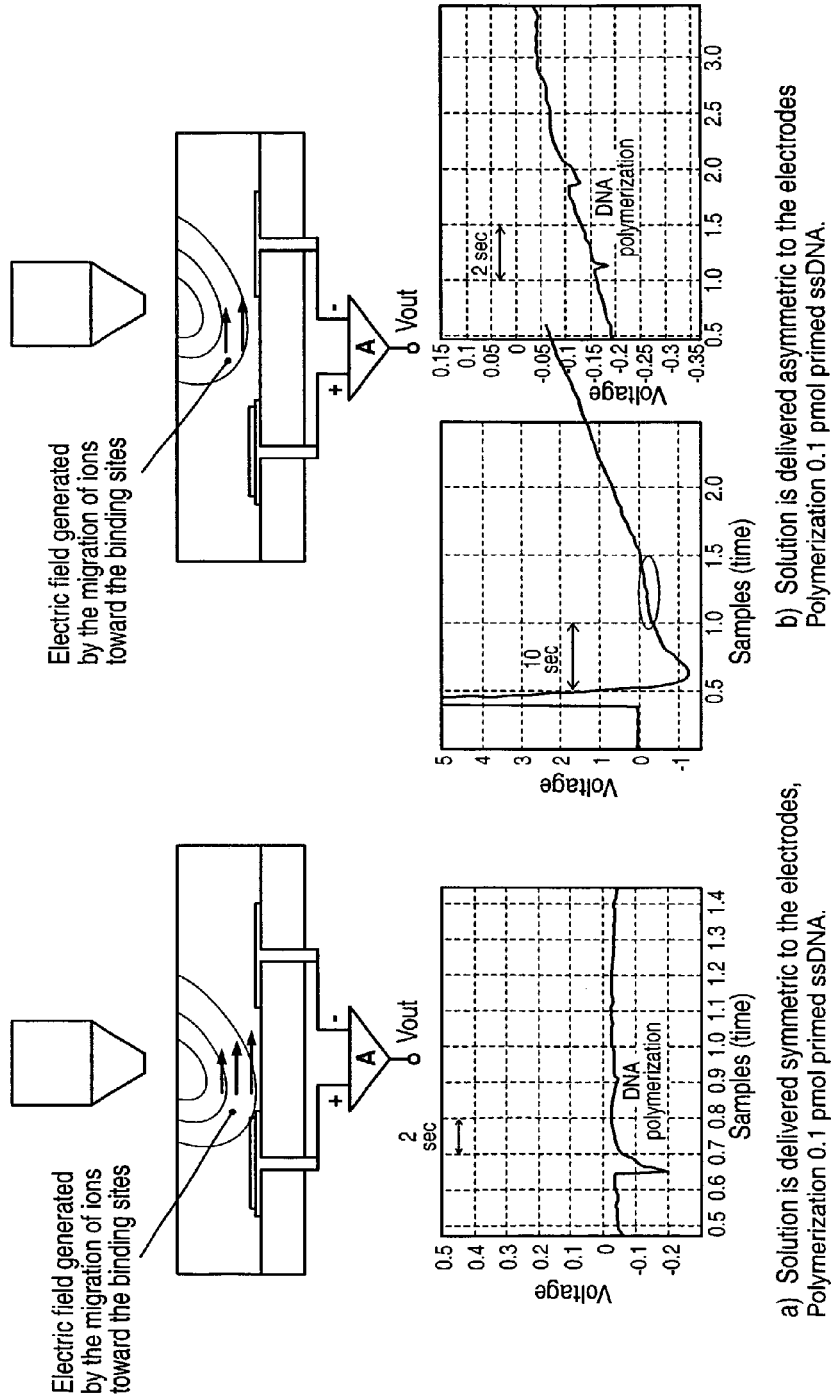

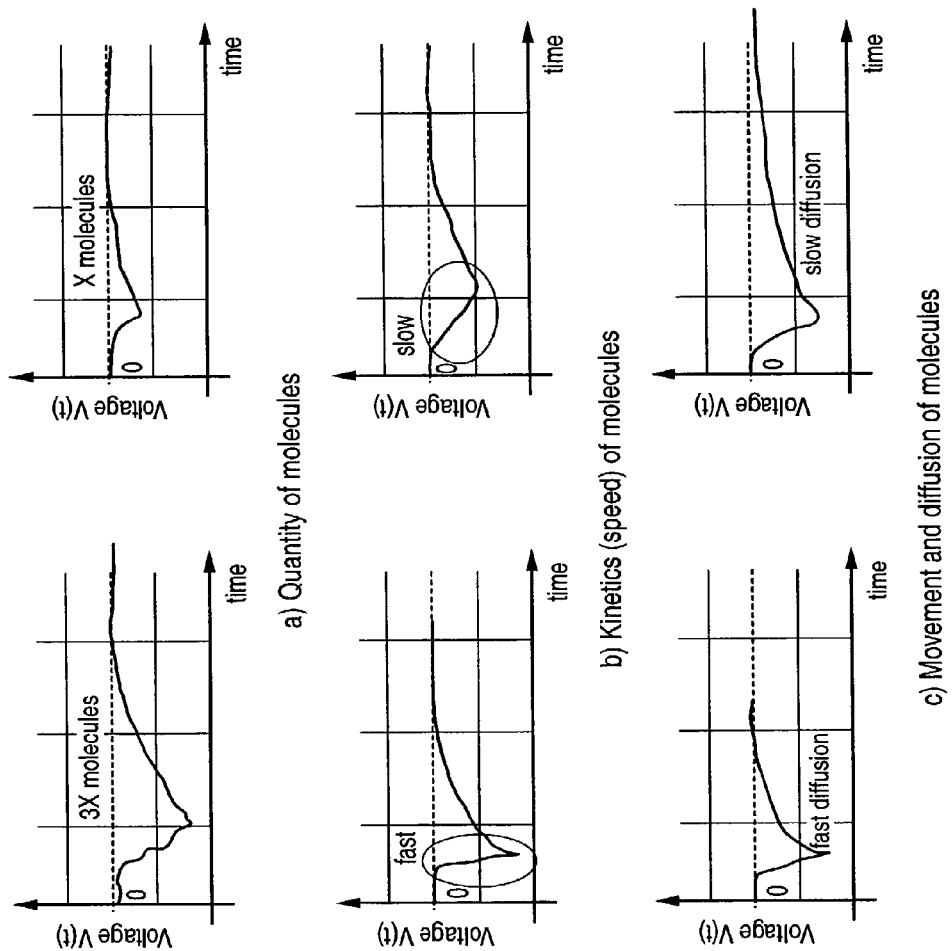
FIG. 2.4

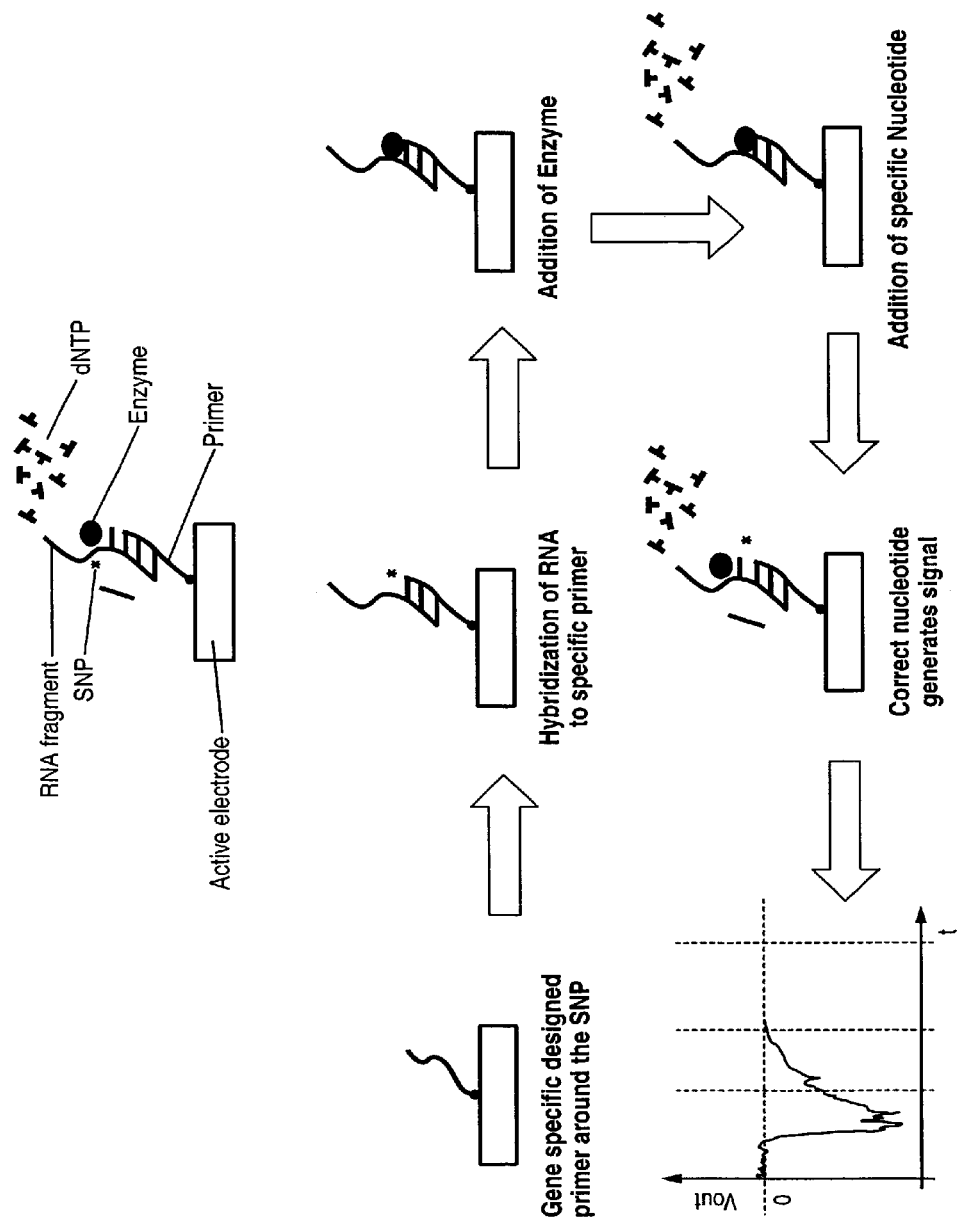
FIG. 4.1

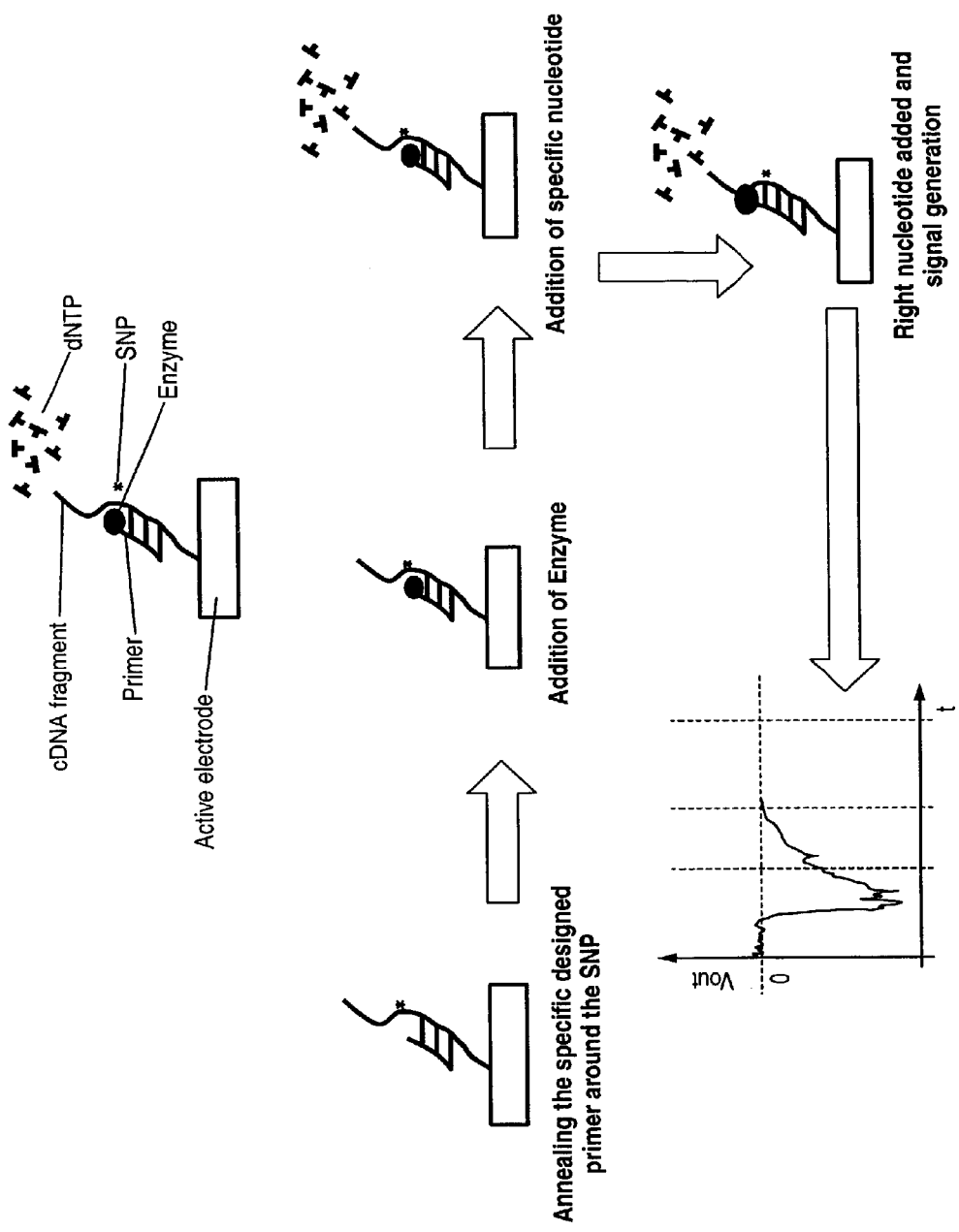
FIG. 4.2

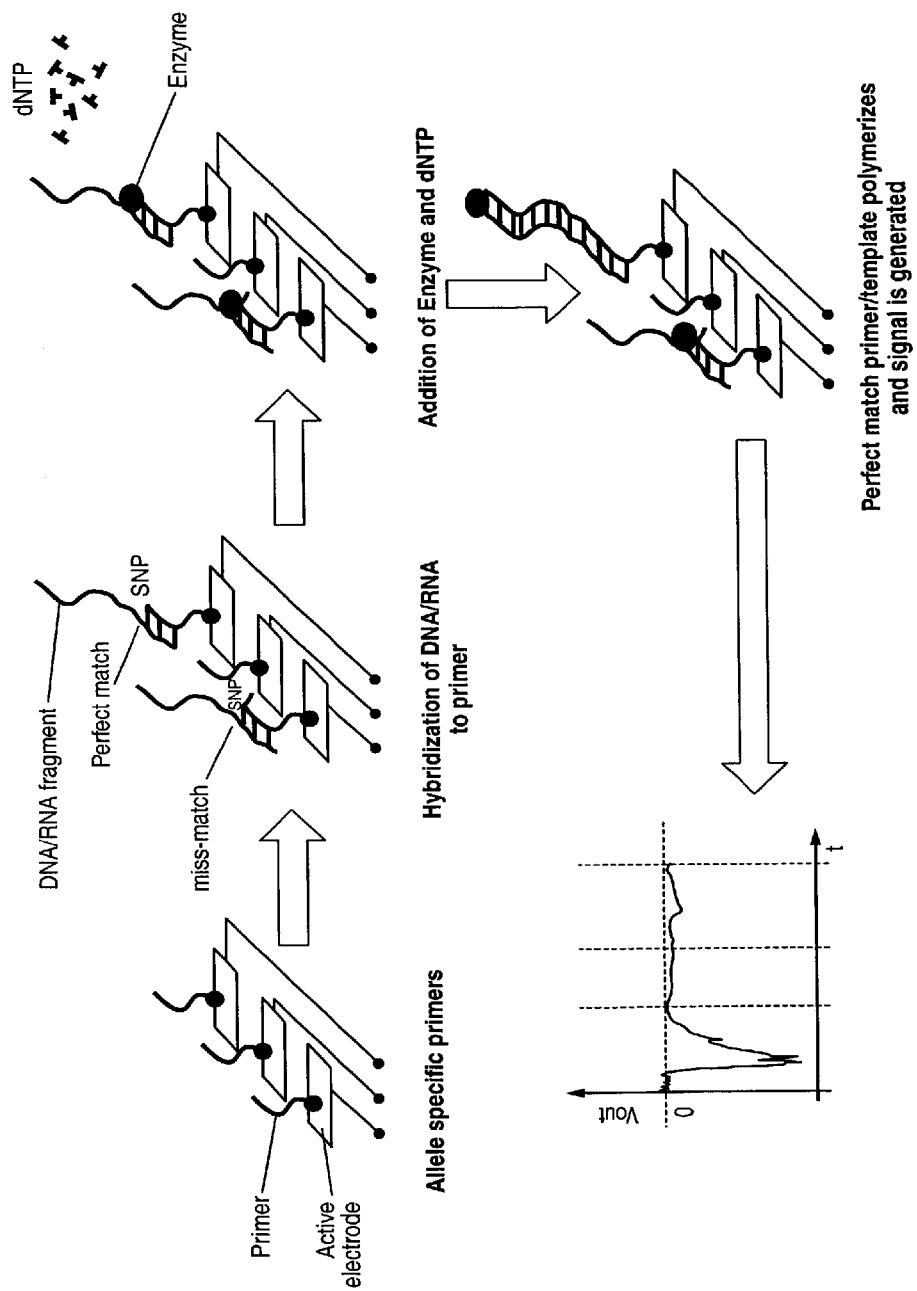
FIG. 4.3

PCR product attracts to an electrode by using a permanent magnet and paramagnetic beads Basic model of the sensor with a differential amplifier Some sample charge sequencing extension signatures for 300 bp DNA

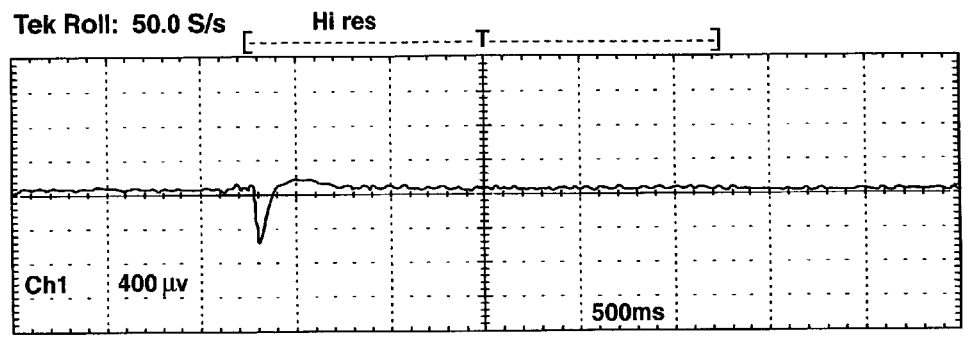
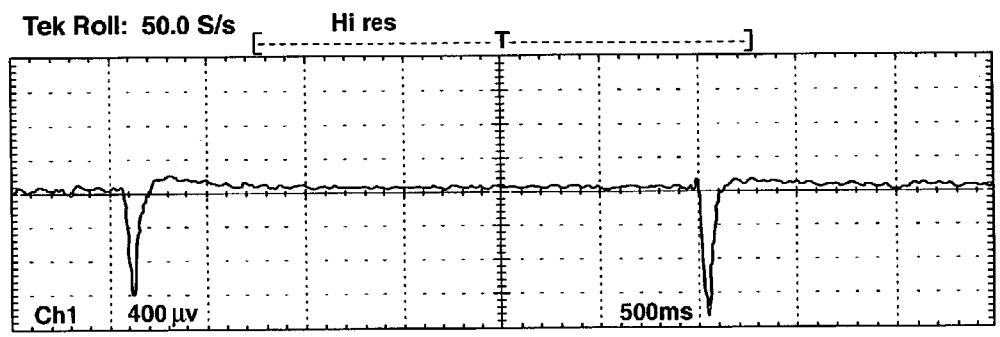
More sample charge sequencing extension signatures for 300 bp DNA with two different concentrations of immobilized DNA (0.05 pmol and 0.1 pmol)
*FIG. 18B*

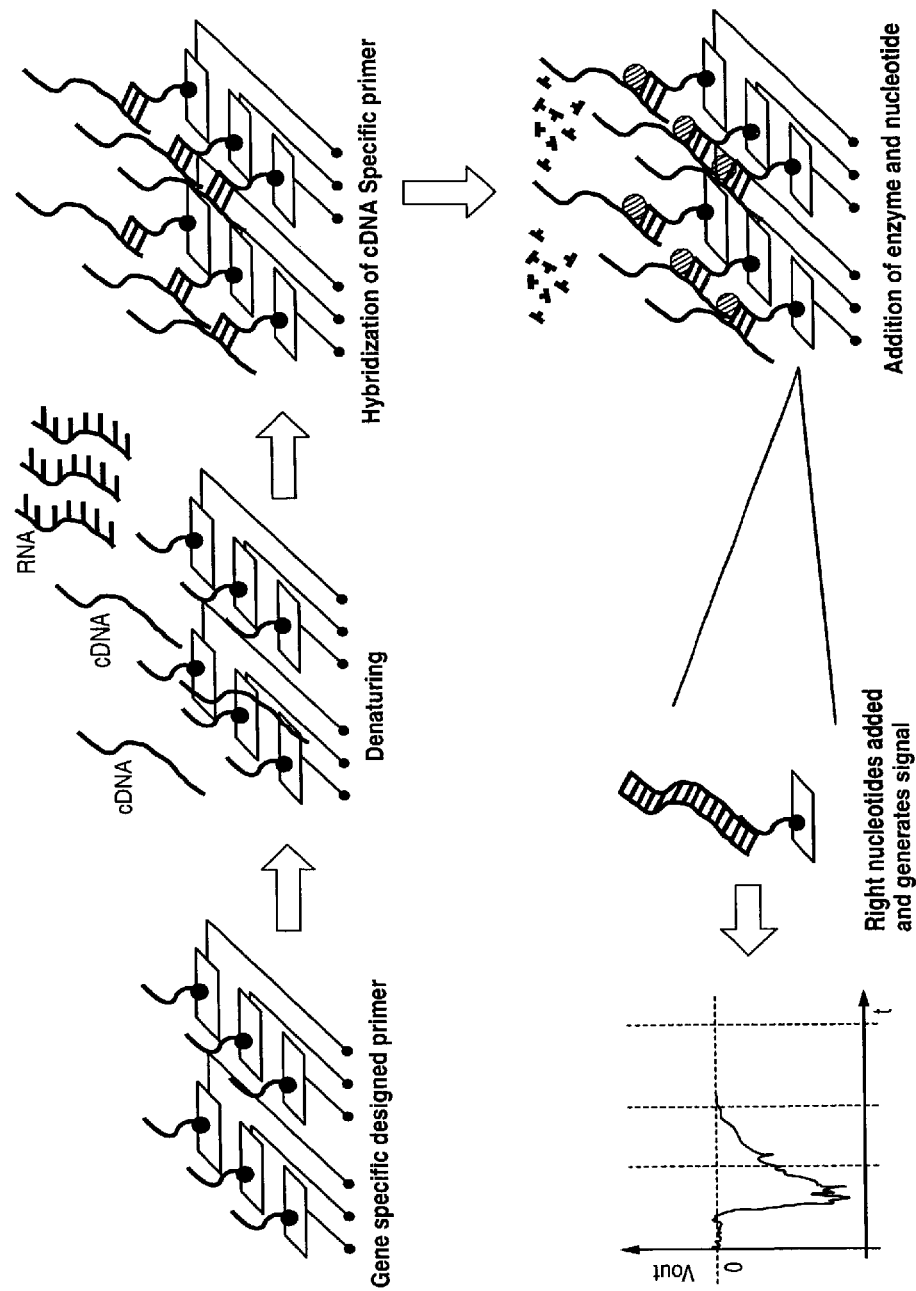

TRANSIENT ELECTRICAL SIGNAL BASED METHODS AND DEVICES FOR CHARACTERIZING MOLECULAR INTERACTION AND/OR MOTION IN A SAMPLE

CROSS-REFERENCE TO RELATED APPLICATIONS

This application is a divisional of application Ser. No. 10/040,303, filed on Oct. 19, 2001, which claimed the benefit under 35 U.S.C. §119(e) of U.S. Provisional Patent Application Ser. No. 60/242,047 filed Oct. 20, 2000 and U.S. Provisional Application Ser. No. 60/285,578 filed Apr. 20, 2001; the disclosures of which are herein incorporated by reference.

INTRODUCTION

Background

There are many applications where one desires to detect and/or characterize a molecular motion and/or interaction, e.g., the occurrence of a binding event (either covalent or non-covalent) between two or more molecules, in a sample. Such applications find use in a variety of different fields, including research and medical, e.g., diagnostic fields. For example, many research and clinical diagnostic protocols are based on the detection of an analyte in a sample using mechanisms in which the presence and/or the quantity of one or more analytes in a sample is detected and/or characterized based on detection of its binding to a complementary binding pair member.

Because of the importance of such applications to such a wide variety of different disciplines, an enormous variety of different protocols and methodologies have been developed to perform such applications. Many protocols and methodologies use detectable labels, where labels can adversely modify the characteristics of a molecule(s) of interest. Some other protocols use indirect chemical or physical measurements to analyze the sample, yet in most of these protocols, either expensive and complicated detection devices must be employed, or sensitivity is quite limited.

As such, there is continued interest in the development of new methodologies for use in the characterization of molecular motion and/or interactions in a sample.

SUMMARY OF THE INVENTION

Transitory electrical signal based methods and devices for characterizing a first molecule and a second immobilized molecule in a sample are provided. In the subject methods, a transient electrical signal generated by monodirectional movement of the first molecule relative to the second immobilized molecule in the sample is detected and related to at least one characterizing feature of the first and second molecules in the sample, e.g., total charge, motion, velocity, quantity, structure, or binding event, where in many embodiments the transient electrical signal which is generated by the excess charge of the first molecule in the vicinity of the second molecule (binding sites) is related to the occurrence of an interaction between the first and second molecules in the sample. The subject methods and devices find use in a variety of applications, including, but not limited to: (1) the detection and/or characterization of polymerase catalyzed template dependent primer extension reactions, e.g., for nucleic acid sequencing, SNP detection, gene expression profiling, real time PCR, etc.; (2) analyte detection applications, e.g., the detection of protein and/or nucleic acid analytes in a sample; and (3) the characterization of molecular motion, e.g. measuring the diffusion length of molecules and/or ions.

BRIEF DESCRIPTION OF THE FIGURES

FIGS. 1.1 and 1.2 provide a schematic representation of the mechanism that gives rise to the transient electrical signal employed in the subject invention.

FIGS. 1.3 (i.e., 1.3.*a* and 1.3.*b*.); 1.4 (i.e., 1.4.*a* and 1.4.*b*) and 1.5 (i.e., 1.5.*a* and 1.5.*b*) provide a number of examples representing the transient signals.

FIG. 2.1 provides a view of a system (i.e., a representative planar sensor system) according to one embodiment of the subject invention.

FIGS. 2.2 and 2.3 provide results of DNA polymerizations with a dual electrode embodiment of the subject invention FIG. 2.4 provides examples of how the transient signal is interpreted to obtain qualitative/quantitative information about A and B in an assayed sample according to the subject invention.

FIGS. 4:1 to 4:3 provide different schematic representations of a SNP detection protocol according to the subject invention.

FIGS. 18A to 18E and 21 provide the results of the sequencing assay reported in the Experimental Section, below.

FIGS. 19A and 19B provide a schematic illustration of a gene expression array assays according to the subject invention.

DEFINITIONS

Figure 3:
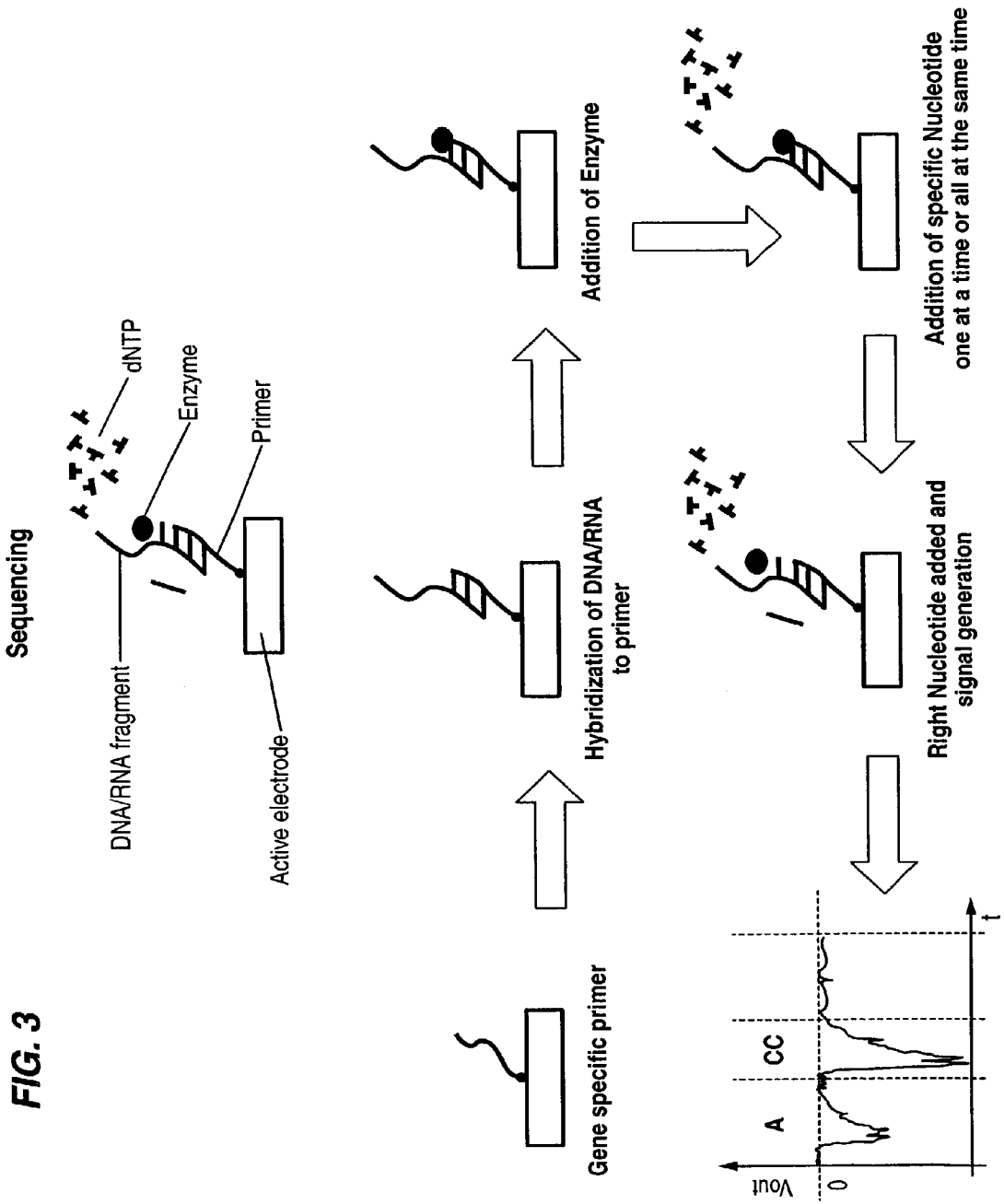
FIG. 3 provides a schematic representation of a sequencing application according to the subject invention.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to up to about 100 nucleotides in length.

The term "polynucleotide" as used herein refers to a single or double stranded polymer composed of nucleotide monomers of generally greater than 100 nucleotides in length and up to about 8,000 or more nucleotides in length. Polynucleotides include single or multiple stranded configurations, where one or more of the strands may or may not be completely aligned with another.

A "nucleotide" refers to a subunit of a nucleic acid and includes a phosphate group, a 5 carbon sugar and a nitrogen containing base, as well as analogs of such subunits.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "array" as used herein means a substrate having a plurality of transitory electrical signal detection elements stably attached to its surface, where the binding agents may be spatially located across the surface of the substrate in any of a number of different patterns and are generally fluidically isolated from one another.

The term "binding agent" means any agent that is a member of a specific binding pair, where such agents include: peptides, e.g. proteins or fragments thereof; nucleic acids, e.g. oligonucleotides, polynucleotides; and the like; etc.

The term "biopolymer" includes peptides or polynucleotides, as well as such compounds composed of or containing amino acid or nucleotide analogs or non-nucleotide groups. As such, this term includes those compounds in which the conventional polynucleotide backbone has been replaced with a non-naturally occurring or synthetic backbone, and those a nucleic acid in which one or more of the conventional bases has been replaced with a synthetic base capable of participating in Watson-Crick type hydrogen bonding interactions.

DESCRIPTION OF THE SPECIFIC EMBODIMENTS

Transitory electrical signal based methods and devices for characterizing a first molecule and a second immobilized molecule in a sample are provided. In the subject methods, a transient electrical signal generated by (i.e., caused by) monodirectional movement of the first molecule relative to the second immobilized molecule in the sample is detected and related to at least one characterizing feature of the first and second molecules in the sample, e.g., total charge, motion, velocity, quantity, structure or binding event, where in many embodiments the transient electrical signal that is generated by the excess charge of the first molecule in the vicinity of the second molecule (binding sites) is related to the occurrence of an interaction between the first and second molecules in the sample. The subject methods and devices find use in a variety of applications, including, but not limited to: (1) the detection and/or characterization of polymerase catalyzed template dependent primer extension reactions, e.g., for nucleic acid sequencing, SNP detection, gene expression profiling, real time PCR, etc.; (2) analyte detection applications, e.g., the detection of protein and/or nucleic acid analytes in a sample; and (3) the analysis of molecular motion, e.g., measuring the diffusion length of molecules and/or ions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

In further describing the subject invention, the methods are described first in greater detail, both generally and in terms of a number of representative applications. Following this section, devices and systems for practicing the subject methods are reviewed in greater detail.

Methods

As summarized above, the subject invention provides methods for characterizing a first molecule and a second immobilized molecule in a sample. In practicing the subject methods, a transient electrical signal generated by the movement of the first molecule (typically a plurality of identical first molecules) relative to an immobilized second molecule (typically a plurality of identical immobilized second molecules) through a medium is employed to characterize the molecules. By "relative to" is meant "towards or away from", such that the subject invention provides methods based on use of a detected transitory electrical signal generated by the movement of a first molecule towards or away from an immobilized second molecule. The movement that causes the detected transitory electrical signal employed in the subject characterization methods is monodirectional. While the movement may be take the form of a linear, curvilinear or other progression pathway through the medium, at no time is the movement backwards. As such, the movement that generates the detected transitory electrical signal is the monodirectional movement of the first molecule towards or away from the immobilized second molecule.

The molecules characterized by the subject invention are present in a sample medium. In many embodiments, the medium is a fluid, gaseous or gel conducting medium in which molecules have finite none-zero mobility, e.g., a fluid aqueous medium, a gel medium made up of an aqueous fluid component and one or more polymeric thickening agents, etc.

The first and second molecules may be a variety of different types of molecules, including small molecule analytes, e.g., haptens, toxins, hormones, etc, monomers, e.g., amino acids and nucleotides, polymers, e.g., polypeptides (such as proteins and fragments thereof, ligands, receptors), polysaccharides, nucleic acids, e.g., deoxyribonucleic acids, ribonucleic acids, including oligonucleotides, polynucleotides, etc. In many, though not all, embodiments, the first and second molecules are the same kind of molecule, e.g., they are both nucleic acids or they are both proteins. In certain embodiments, the second molecule is a polymer and the first molecule may or may not be a polymer. Specific second or immobilized molecules of interest include, but are not limited to: nucleic acids, e.g., DNA or RNA oligo- or polynucleotides, as well as duplex structures containing the same; proteins, e.g., antibodies or binding fragments thereof; receptors, etc. In many instances, the first and second molecules are ions, or at least include ionized moieties that carry local charges even if the overall net charge of the medium is zero.

As mentioned above, the subject methods are methods of characterizing the first and second molecules in a sample. By characterize is meant determining information about at least one characterizing feature of the first and second molecules in the sample, e.g., the local charge of the molecules, the motion of the molecules, the velocity of the molecules, the quantity of the molecules, the structure of the molecules, a binding event between the molecules, a dissociation of the molecules, etc. In many embodiments, the subject methods are methods of characterizing an interaction between the molecules, i.e., a binding event (e.g., a covalent or non-covalent binding between the molecules) or dissociation event between the molecules.

A feature of the subject invention is that the at least one characterizing feature of the first and second molecules in the sample is determined by: (a) first detecting a transient electrical signal generated by (i.e., caused by, resulting from, etc.) the movement of the first molecule relative to the second molecule through the conducting medium sample; and then (b) relating the detected transient electrical signal to the at least one characterizing feature of the first and second molecules in the sample, e.g., the occurrence of a binding event between, or dissociation of, the first and second molecules in the sample. By transient electrical signal is meant a non-permanent, detectable electrical parameter generated by movement of the first molecule relative to the second through the conducting medium. As the electrical signal of interest is transient, it necessarily only exists for a limited period of time. In many embodiments, this period of time generally ranges from about 1 minute to about 1 microsecond, usually from about 5 second to about 10 milliseconds. In addition, the transient electrical signal of interest is not a steady state signal, but is instead a signal that changes over time. In other words, the signal or parameter that is detected and employed to detect and/or characterize the movement of the first molecule relative to the second through the conducting medium, as described in greater detail below, is a differential signal or parameter that is observed over a detection period, as described above, and can also be referred to as a transient electrical signature, where the transient electrical signature is one that is generated or caused by (i.e., results from) the movement of the first molecule relative to the second in the conducting medium. A variety of different detectable transitory electrical signals/parameters may be employed in the subject methods. Non-limiting examples of such signals include, but are not limited to: voltage, charge, current, impedance, etc. As indicated above, the signals that are measured are transitory and changing over the measurement period.

The transitory electrical signal whose presence is employed in the subject methods is generated by the monodirectional movement of the first molecule(s) through the sample medium relative to the second immobilized molecule(s), as further explained in reference to FIG. 1.1 through FIG. 1.5. FIGS. 1.1 and 1.2 show a second molecule A (actually a plurality of second molecules A) and first molecule B (actually a plurality of first molecules B) in a fluid conducting medium when second molecule is mobile and the first molecule is immobilized respectively. J is the net current density of B. When binding between A and B occurs, if both A and B are free in the solution, the net movement, and therefore J, is zero. (See FIG. 1.1) On the other hand, when A is immobilized, because B is captured by the binding site of A and becomes immobilized itself, a diffusion gradient of B toward A is produced, and therefore a none-zero J. (See FIG. 1.2) If B has some charge (e.g. B is a dNTP ion), J generates both a transient electrical potential and a transient electrical charge in the medium, which creates "signals/parameters" that are both detectable. These detectable signals/parameters are transient because counter ions eventually move toward the localized charge to shield it and take the system back to equilibrium. FIGS. 1.3 to 1.5 show some examples of the voltage created by this phenomenon.

Generally, the transitory electrical signal or parameter of interest is detected by monitoring the sample medium of interest for the transitory electrical signal. The sample medium of interest is generally of a defined volume that includes both the first molecule and immobilized second molecule. The defined volume may vary, but typically ranges from about 5 nano liter to about 2 ml, usually from about 5 µl to about 0.1 ml and more usually from about 10 µl to about 0.05 ml. More specifically, a defined volume of medium, as described above, that includes the first and second molecules is monitored for the transitory electrical signal of interest.

In practicing the subject methods, the defined volume of medium may be monitored to detect the transitory electrical signal of interest using any transitory electrical signal detection element, where in many embodiments the detection element that is employed is an electrode detection element, which electrode detection element includes at least one working electrode. The working electrode has the second molecule immobilized on its surface. The electrode(s) may be fabricated from any convenient material(s), which materials include metals, conductive polymers, carbon, silicon, poly-silicon and the like. The electrode(s) can also be covered with thin isolators like glass, quartz, etc. Any convenient surface attachment technology may be employed for immobilizing the second molecule on the surface of the working electrode, where the particular surface attachment chemistry employed may vary depending on the nature of the surface and the second molecule, where representative surface attachment technologies include covalent attachment, sometimes through linker groups, non-covalent attachment, including both chemical, e.g., specific binding pair member, and non-chemical, e.g., magnetic force (such as paramagnetic beads on a magnetized working electrode), etc. In many embodiments, the electrode detection includes, in addition to the working electrode, a reference electrode, where the reference electrode may be made from a variety of different materials and present in a variety of different configurations. In certain embodiments, the electrode detection element includes a plurality of different electrodes. The electrodes of the electrode detection element may be configured in a variety of topologies, relative to each other, so long as they are capable of monitoring the sample in contact therewith for the requisite transitory electrical signal generated by the movement of the mobile molecules through the sample medium relative to the immobilized molecule(s). Where the electrode detection element includes both a working and reference electrode, as well as other electrodes, the electrodes may or may not have substantially the same, if the not the same, surface area in contact with the sample. While the surface area of each electrode may vary, it typically ranges from about 10 cm$^2$ to about 1 µm$^2$, usually from about 4 mm$^2$ to about 0.01 mm$^2$. Where the two electrodes have surface areas that are substantially the same, the surfaces areas of electrodes are considered to be substantially the same if they vary from each other by no more than about 10%, usually no more than about 2%.

In many embodiments, the noise reduction element is employed within the electrode topology and sensor, where the electrode array is capable of removing the unwanted noise component from the detected transient electrical signal, to provide a noise depleted signal that is then employed in the characterization step, as described in greater detail below. For example, in many embodiments, a differential amplifier is employed, e.g., a differential voltage or current amplifier, which receives input from the working and reference electrodes and provides a relatively or substantially noise depleted output signal. A detailed representative embodiment of a system of the subject invention is shown in FIG. 2.1. In FIG. 2.1, the displayed system includes volume of conducting medium sample 17. Present in the conducting medium are first molecules in solution, which are moving relative to, e.g., towards, immobilized second molecules A. Also shown is electrode detection element 16, which is made up of a first working electrode 16a and a second reference electrode 16b, where the immobilized second molecules B are immobilized on the surface of first electrode 16a.

In FIGS. 2.2 to 2.3, the actual results of the FIG. 2.1 planar topology two electrode system are shown. In FIG. 2.2 molecule A (0.1 pmol ssDNA) is not active (no primer), so addition of molecule B (dNTP) in the presence of the enzyme creates no polymerization signal, but in FIG. 2.3 molecule A is made active (by adding primer) which creates the binding sites and therefore the detectable transitory electrical signal.

The system and electrode detection element thereof shown in FIG. 2.1 is merely one representative embodiment of the devices and systems of the subject invention. The electrode detection element employed in the subject methods may take a variety of different formats, where additional representative formats are described in greater detail below.

In many embodiments, however, the devices or apparatuses employed to practice the subject methods are devices that include at least a first working electrode having the second molecule immobilized thereon, a driver for the working electrode (and any other electrodes present on the device)(e.g., a differential amplifier to create a charge difference between the working and reference electrode in a medium in contact therewith) and a signal processor for evaluating a response from the working electrode and generating a transient electrical signal based thereon. In many embodiments, the device further includes at least one reference electrode and the signal process evaluates the responses from both the working and reference electrode and compares them to generate the transitory electrical signal. In many embodiments, the device further includes a medium containment means in which the one or more electrodes may be contacted with a medium present in the medium containment means.

In operation, the transitory electrical signal detection element may be "passive" or "active." Passive detection elements are elements that merely passively observe or monitor the medium for the transitory electrical signal, and do not impart any stimulus to the medium and/or detection element components. Alternatively, active detection elements are elements that impart a stimulus to the medium and/or detection element being monitored in the process of detecting the transitory electrical signal. Examples of such various stimuli of interest employed in active detection elements include, but are not limited to: injected current, voltage disturbance, electrochemical disturbance, etc. Regardless of whether the detection element is active or passive, it provides a detection of the transitory electrical signal/parameter caused by the movement of the first molecule in the medium relative to the second, immobilized molecule.

In the subject methods, following the detection of the transitory electrical signal of interest, as described above, the detected signal is then related to at least one characterizing feature of the first and second molecules in the sample, as described above. In other words, the detected transitory electrical signal is evaluated to make a determination about a characteristic of the first and second molecules in the sample, e.g., whether they have interacted, e.g., bound to or dissociated from each other. The determination may be qualitative or quantitative, in the sense that in certain embodiments the magnitude of the detected transitory signal is proportional to the amount or number of first molecules that interact with the second or immobilized molecule(s) in the sample. FIG. 2.4 shows some examples of analyzing the transient signal. For example, FIG. 2.4.*a* shows how the quantity of molecules interacting impacts the observed transient electrical signal. As such, the observed transient electrical signal can be employed to determine the quantity of molecules that are interacting. FIG. 2.4.*b* shows how the kinetics of the interaction impacts the observed signal. Thus, the observed signal can be employed to determine the kinetics of the interaction. FIG. 2.5.*c* shows how the movement and diffusion of the molecules impacts the observed signal. As such, the observed signal can be employed to determine the movement and diffusion of the molecules in the sample. The detected signal or waveform that is detected by the sensor may be analyzed in time and/or frequency. This relating step provides information about the at least one characteristic feature of the first and second molecules in the sample that is being assayed.

The resultant information of at least one characterizing feature of the first and second molecules in the sample may be employed in a number of different ways in a number of different applications. For example, the detected interaction of the first and second molecules based on the detected transitory electrical signal generated by movement of the first molecule relative to the second may be used to determine the presence of an analyte of interest in the medium, where the determination may be qualitative or quantitative, since the detected signal in many embodiments is proportional in intensity to the amount of analyte in the sample whose movement gives rise to the detected transitory electrical signal. (See e.g., FIG. 2.4) In these embodiments, the detected movement is related to the occurrence of a binding event, i.e., a binding event between the first molecule and second immobilized molecule. In other embodiments, the detected movement is employed to obtain information about the occurrence of, and or more specifically characterize, a template dependent polymerization reaction, e.g., a polymerase mediated template dependent primer extension reaction in which the immobilized second molecule is a template/primer nucleic acid duplex and the first molecule is a nucleotide. These representative categories of the subject methods and representative specific applications/protocols in which they find use are further described below.

Detection/Characterization of Template Dependent Primer Extension Reactions

In many embodiments, the at least one characteristic feature that is obtained using the subject methods is the detection of a polymerase mediated template dependent primer extension reaction between a first nucleotide molecule and a second immobilized template/primer nucleic acid duplex molecule. By polymerase mediated template dependent primer extension reaction is meant a polymerization reaction in which a nucleotide is covalently attached in a polymerase catalyzed reaction to the 3' end of primer containing nucleic acid hybridized to a template nucleic acid, where the particular nucleotide that is covalently attached to the end of the primer nucleic acid is one that is the complement of the corresponding nucleotide base in the template nucleic acid, e.g., A with T, C with G, etc. Template dependent primer extension reactions are well known to those of skill in the art, where representative embodiments include those described in U.S. Pat. Nos. 4,683,202; 4,683,195; 4,800,159; 4,965,188 and 5,512,462, the disclosures of which are herein incorporated by reference. As is well known in the art, the template and primer nucleic acids may be RNA or DNA, the nucleotides may be ribo- or deoxyribonucleotides, and the polymerase may be selected from a number of different polymerases, including DNA polymerases, RNA polymerases and reverse transcriptases, where the particular selection of any of the specific components is made using selection criteria well known to those of skill in the art.

In these embodiments, the first molecule is a nucleotide and the immobilized second molecule is actually a duplex nucleic acid made up of the template nucleic acid that is hybridized to a primer containing nucleic acid, e.g., a primer or primer containing nucleic acid that has been at least partially extended by the previous addition of one or more nucleotides. In the primer extension reaction, a polymerase, e.g., polymerase or reverse transcriptase, catalyzes the addition of the nucleotide to the primer nucleic acid of the immobilized duplex nucleic acid molecule. The movement of the nucleotide through the medium towards the immobilized duplex generates a detectable transient electrical signal that is created by the accumulated local charge and is related to the interaction, i.e., covalent attachment, of the nucleotide to the primer in the template dependent primer extension reaction. As such, the transient electrical signal observed in the medium provides an indication of whether or not a specific interaction between the first and second molecules occurs, i.e., whether or not a primer extension reaction occurs in the medium. In other words, by monitoring the medium for a transient electrical signal and gathering of a transient local charge around the template, one can know whether or not a template dependent primer extension reaction is occurring in the medium, and specifically at the immobilized template/primer duplex in contact with the medium. Furthermore, depending on the particular application protocol, one can characterize a template dependent primer extension reaction in terms of the specific sequence in which different nucleotides are added to the 3' end of the primer nucleic acid. The rate of the reaction is different for different nucleotides, i.e., is nucleotide dependent, so the movement of the different nucleotide molecules toward the template is going to be dependent on the template directed incorporation of the nucleotides, which feature can be detected in the observed transient signal.

In certain embodiments, the transient electrical signal observed in the medium is employed to determine the occurrence of a single nucleotide addition to the 3' end of a primer nucleic acid in a template dependent primer extension reaction. In these embodiments, a system is provided that is made up of the medium, the electrode detection system and the immobilized template nucleic acid/primer nucleic acid duplex, which in many embodiments is immobilized on a surface of one of the electrodes of the electrode detection element. For example, in the representative system depicted in FIG. 2.1, electrode 16a of the electrode detection element 16 has on a surface thereof template/primer duplexes denoted as B. The immobilized template/primer duplex may be immobilized on the surface of the electrode using any convenient protocol, e.g., through covalent or non-covalent attachment, via magnetic attraction using magnetic beads as linkers, and the like. Using any convenient protocol, e.g., by introducing, e.g. by contacting, the electrode 16a into a medium 17 containing the appropriate nucleotide or by introducing the appropriate nucleotide into a medium already in contact with electrode 16a, the medium of the system is made to include a nucleotide. If the nucleotide is the correct nucleotide to add to the 3' end of the primer nucleic acid as dictated by the template, a transient electrical signal and local charge is generated in the medium. Conversely, if the nucleotide is not the correct nucleotide, no transient electrical signal is generated in the medium. As such, the detection of a transient electrical signal provides an indication that a primer extension reaction has occurred between the introduced nucleotide and the primer of the immobilized primer/template duplex.

The above described methods of detecting single nucleotide additions in template dependent primer extension reactions find use in a variety of different applications. Specific representative applications of interest include nucleic acid sequencing, single nucleotide polymorphism (SNP) detection, microbial, e.g., pathogenic, detection, etc.

For purposes of illustration, each of these representative applications is now described in greater detail below.

In nucleic acid sequencing applications, the above described protocol is employed to determine the addition, one at a time, of a nucleotide to a primer nucleic acid and thereby determine the sequence of the template nucleic acid in the immobilized template/primer nucleic acid duplex. In these embodiments, the immobilized template/primer duplex having the template to be sequenced is sequentially contacted with successive mediums that include a single nucleotide or dNTP (e.g., dCTP, dTTP, dATP, dGTP) (with sufficient washings occurring between each contact to remove unbound nucleotide) and the transitory electrical signal or absence thereof is determined for each contact. Based on the sequence of observed transient electrical signals and knowledge of the specific dNTP content of the successive mediums generating each of the successive signals, the sequence of the template of the immobilized duplex is determined. For example, where the template nucleic acid has a sequence of AGTC, the immobilized duplex containing the template is first contacted with a medium that includes only T. The occurrence of the transitory electrical signal indicates that T is covalently attached to the 3' end of the primer and therefore that the first base at the 5' end of the template is A. If, on the other hand, the duplex is first contacted with a medium that includes only A, no signal is observed and a conclusion is drawn that the first base at the 5' end of the template is not T. By contacting with appropriate nucleotides at each step of the sequence determination protocol, the sequence of the template is readily determined based on the pattern of transient electrical signals, or lack thereof, that is observed. In those embodiments where two nucleotides of the same base are adjacent in the template nucleic acid, the addition of the two complementary nucleotides dictated thereby yields a transient electrical signal that is different, e.g., in time and magnitude, from that generated by a single nucleotide addition. See e.g., FIG. 2.4. Therefore, the same base dinucleotide portion of the sequence can be readily elucidated. In an analogous fashion, the sequences of three or more bases that are the same can be elucidated by appropriately interpreting the transient electrical signal generated thereby. In this manner, the sequence of a given nucleic acid can be readily determined by interpreting a series of sequence transitory electrical signals generated by contacting a duplex that includes the template nucleic acid to be sequenced with a sequential series of mediums each comprising a single dNTP. In these embodiments, either the template or primer of the duplex may be physically attached or immobilized to a substrate, e.g., an electrode surface, in the system employed in the method.

In a variation of the above single nucleotide addition protocol, in certain embodiments, the immobilized duplex is contacted with a medium that includes all four potential dNTPs. In this embodiment, the transitory electrical signal that is generated is one that is unique depending on the sequence of added nucleotides, as each type of added nucleotide provides its own unique contribution to the observed transitory electrical signal, because the rate of the polymerization which modulates the movement of molecules toward the template is different for each nucleotide. For example, the addition of dATP provides a certain unique contribution to the overall observed signal, and the addition of the other three nucleotides each provide a similarly unique contribution to the overall observed signal. Thus, the observed signal will be dependent on the sequence by which the nucleotides are incorporated, and therefore can be used to directly read the sequence of the template strand that is dictating the order in which the nucleotides are covalently bonded to the 3' end of the primer containing nucleic acid. (This method of sequencing is also referred to herein as the "run-off" mode).

A schematic of a representative sequencing protocol according to the subject methods in which a nucleic acid is sequenced is provided in FIG. 3. In FIG. 3, a sample comprising a nucleic acid to be sequenced is first obtained. The nucleic acid is denatured and then immobilized to the electrode of a system according to the subject invention, either before or after hybridizing an appropriate primer to the nucleic acid, e.g., a primer that hybridizes to a universal sequence introduced at the 3' end of the PCR product template during PCR product generation. In FIG. 3, the resultant duplex is immobilized on the electrode surface via covalent attachment of the 5' end of the gene specific primer. The resultant immobilized duplex nucleic acid is then contacted with a reaction buffer, polymerase and one or more dNTPs, as described above. The resultant observed transitory electrical signal, made up of one or more series of transitory electrical signals, depending on the particular sequencing protocol employed (e.g., one where sequential reaction buffers of a single nucleotide are contacted with the duplex (i.e. a single nucleotide method) or where a single reaction buffer with all four nucleotides is contacted with the immobilized duplex (i.e., run-off mode) is then employed to determine the sequence of the template PCR product strand. Instead of a PCR product, the target nucleic acid to be sequenced may also be a RNA isolated directly from an initial sample. In these embodiments, isolated RNA from an initial sample is contacted with a primer specific therefore immobilized on an electrode surface. (See e.g., FIG. 3) The resultant duplex is then contacted with reaction buffer, polymerase and dNTPs as described above. This method may be modified to convert the initial RNA to cDNA, followed by immobilization, contact with a specific primer to produce the primer/template duplex, and then contact with reaction buffer, polymerase and dNTPs as described above.

Another application in which the subject invention finds use is in single nucleotide polymorphism (SNP) detection. In these embodiments, a sample is assayed for the presence of a SNP. The sample may be any convenient sample, and is typically a fluid sample obtained from a host to be assayed for the presence of the SNP, e.g., a mammalian host (including but not limited to pets, livestock, humans etc.), where the fluid sample may be a biological fluid, a fluid prepared from a tissue sample, e.g., a cell lysate, etc., so long as the sample contains the SNP of interest, if present.

Figure 5:
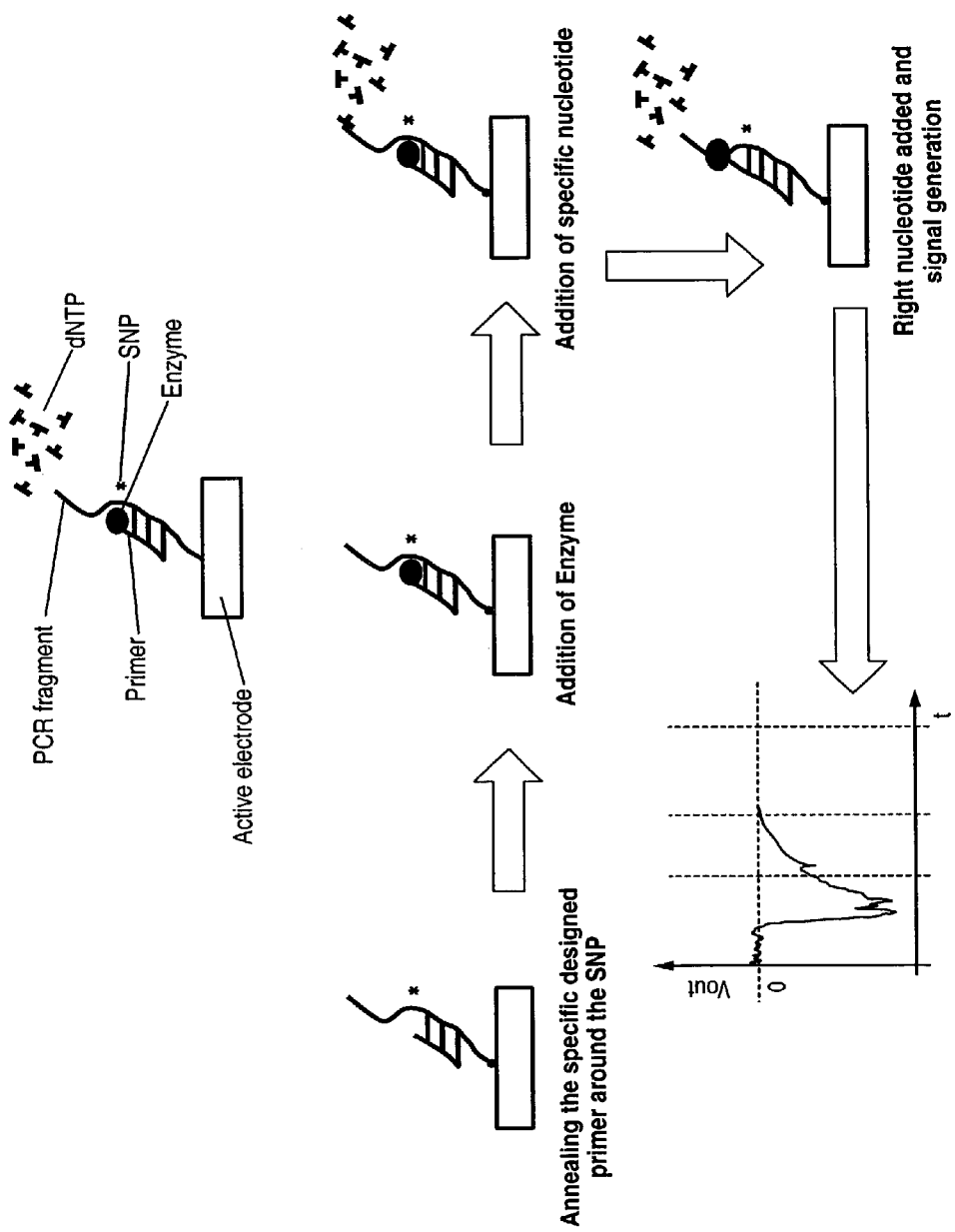
FIG. 5 provides a schematic representation of an alternative SNP detection protocol in which a PCR product that includes an SNP sequence of interest is detected.

FIGS. 4.1 to 4.3 provide schematic representations of three different representative SNP detection protocols. In the embodiment of FIG. 4.1, a suitable sample to be assayed is first obtained. Following total RNA extraction, in one embodiment as represented FIG. 4.1, the extracted RNA is contacted with immobilized primer which hybridizes to the target RNA at the position immediately 5' of the particular variable nucleotide of the SNP (i.e., the primer is an SNP specific primer). The resultant immobilized SNP specific RNA duplex is then contacted with reaction buffer, polymerase and the appropriate dNTP that will attach to the 3' end of the primer if the SNP is present, and thereby provide a transitory electrical signal. A variation of this method is provided in FIG. 4.2. The protocol illustrated in FIG. 4.2 differs from the one shown FIG. 4.1 in that the extracted RNA is first processed into cDNA, e.g., by using standard cDNA synthesis protocols. The resultant cDNA is immobilized on the electrode and then denatured. The SNP specific primer is then hybridized to the immobilized cDNA strand to provide the immobilized duplex, which is then contacted with the reaction buffer, polymerase and dNTP as described above. FIG. 4.3 shows an analogous SNP detection protocol formatted for high throughput applications. FIG. 5 shows a variation of the above SNP detection protocols where the sample is first processed to produce a PCR product that contains the SNP of interest, if present in the initial sample. The PCR product, obtained using standard PCR protocols and appropriate primers, e.g., that flank the region of the initial nucleic acids containing the SNP of interest, is first denatured. The resultant PCR product is then immobilized to the electrode surface. Either prior to or following immobilization, the PCR product strand is hybridized to the SNP specific primer. The resultant immobilized duplex is then contacted with reaction buffer, polymerase and dNTP, and any resultant transient electrical signal, or absence thereof, is related to the presence or absence of the SNP of interest in the sample.

Figure 6:
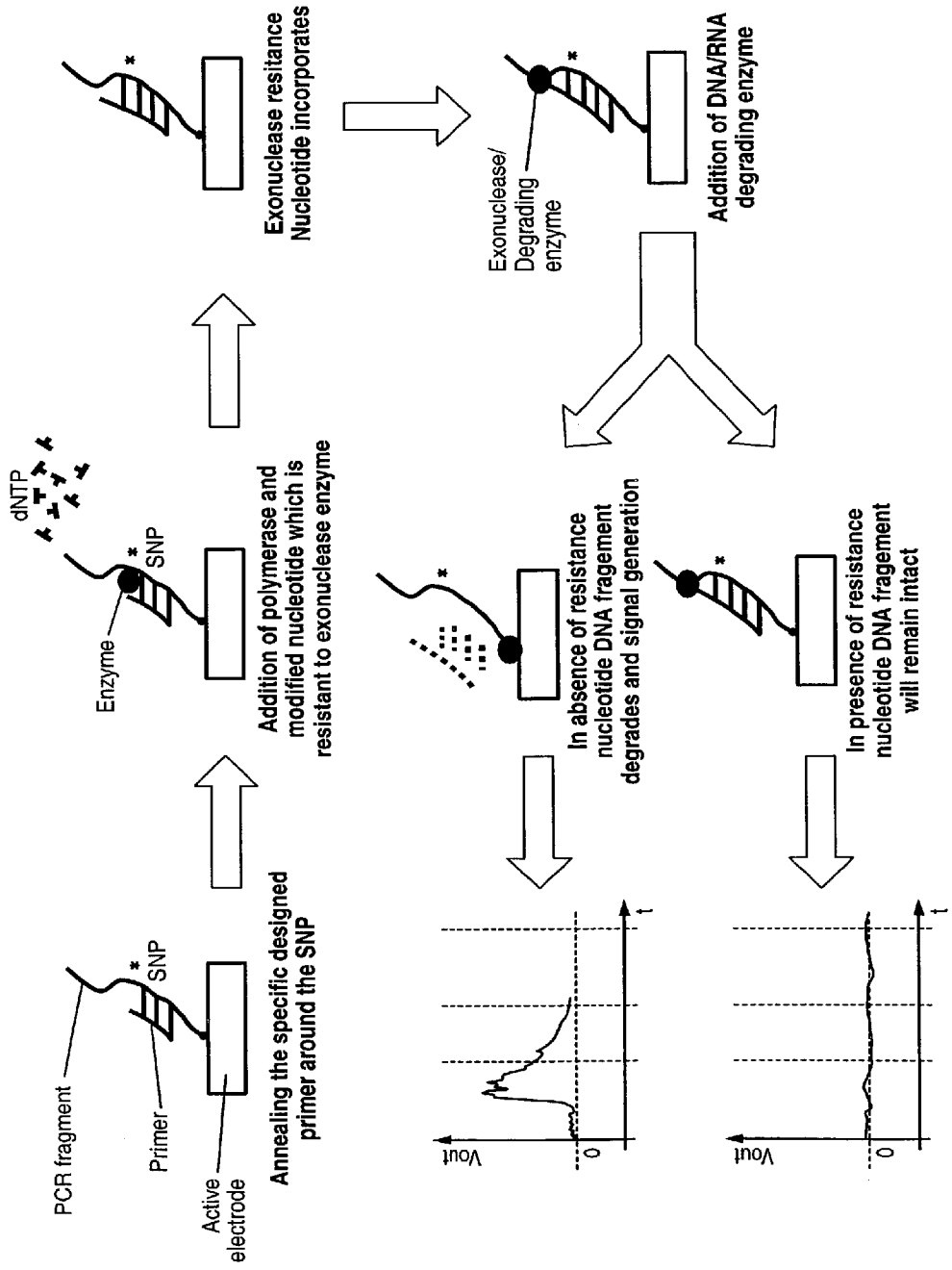
FIG. 6 schematically illustrates another SNP detection protocol according to the subject invention.

A variation of the above described SNP detection protocols is illustrated in FIG. 6. In FIG. 6, an immobilized duplex is first produced, where the immobilized duplex includes both a template DNA strand that is to be assayed for the presence of the SNP and a SNP specific primer (i.e. a primer that hybridizes to the template in a manner such that the next nucleotide added to the 3' of the primer is one that is the complement of the SNP, if present) hybridized to the template. Next, polymerase and an exonuclease resistant dNTP, e.g., thiophosphate-modified nucleotides such as 2'-deoxynucleoside 5' alpha-[P-thio-] (dNT$^s$P) or boranophosphates (2'-deoxynucleoside 5'-alpha-[P-borano-]triphosphates) (dN$^b$TP), etc., that is the complement of the SNP base of interest is contacted with the duplex under primer extension conditions, such that when the SNP is present, the exonuclease resistant dNTP is covalently attached to the 3' end of the primer. Next, the system is contacted with an exonuclease that cleaves from the 3' end but is incapable of cleaving the exonuclease resistant dNTP. Cleavage results in movement of nucleotides away from the immobilized duplex and a concomitant transitory electrical signal. Thus, the absence of an observed transitory electrical signal is equated with the presence of the target SNP of interest, while observation of the transitory electrical signal is equated with the absence of the SNP.

Figure 7:
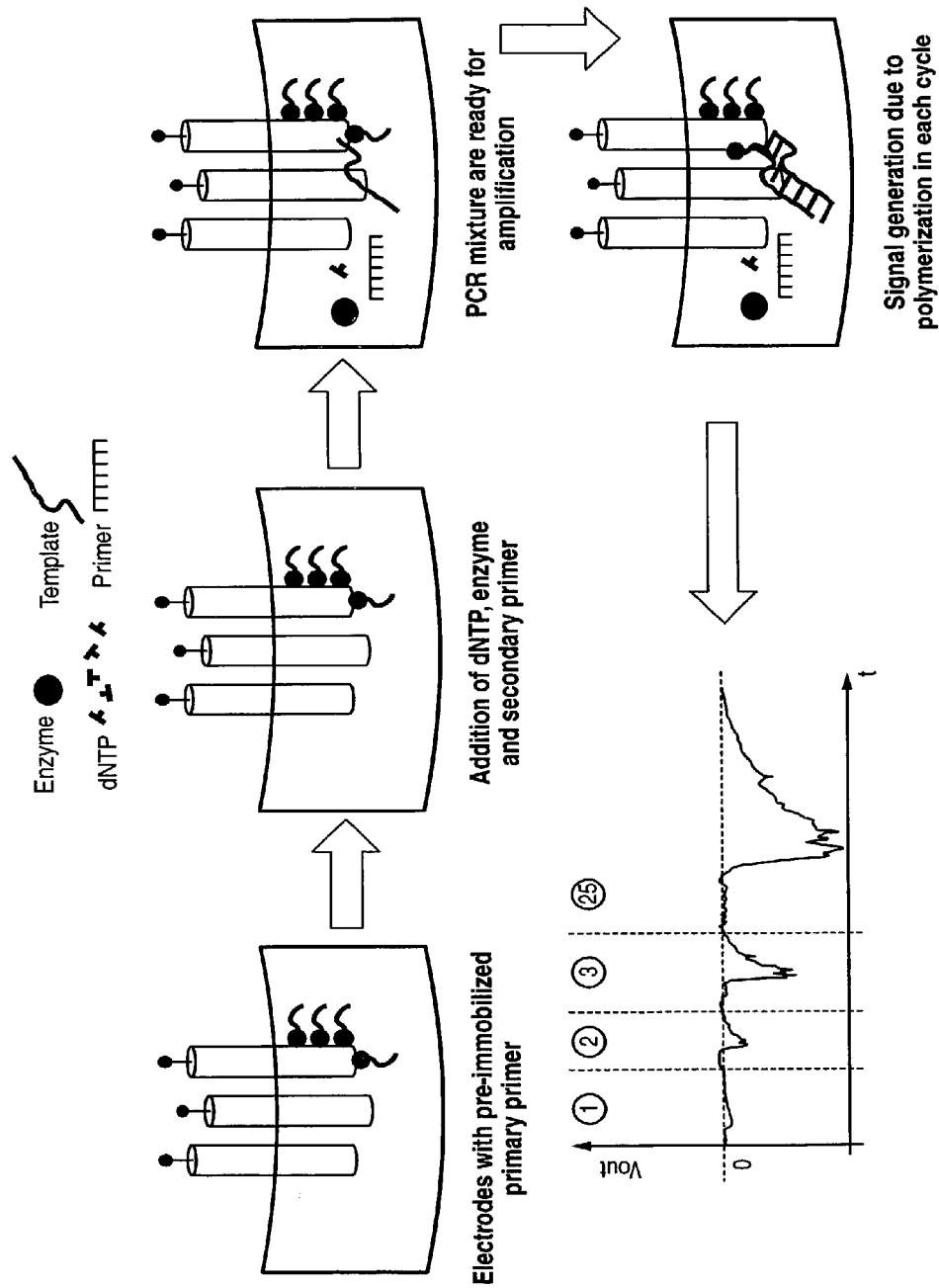
FIG. 7 schematically illustrates a real time PCR application according to the subject invention.

In yet another embodiment, the subject methods may be employed to perform real time PCR applications, as schematically illustrated in FIG. 7. The quantification of amplified target in a polymerase chain reaction (PCR) is achieved by immobilization of one of the two primers onto the electrode and providing contact of the immobilized primer with the template, the other primer, the enzyme and all four dNTPs (i.e., GTP, ATP, TTP and CTP) in the mixture. When nucleotides are added and extension occurs, the electrostatic response in each cycle creates a unique waveform which can be used to evaluate/estimate the mass of the molecules for each cycle.

Figure 8:
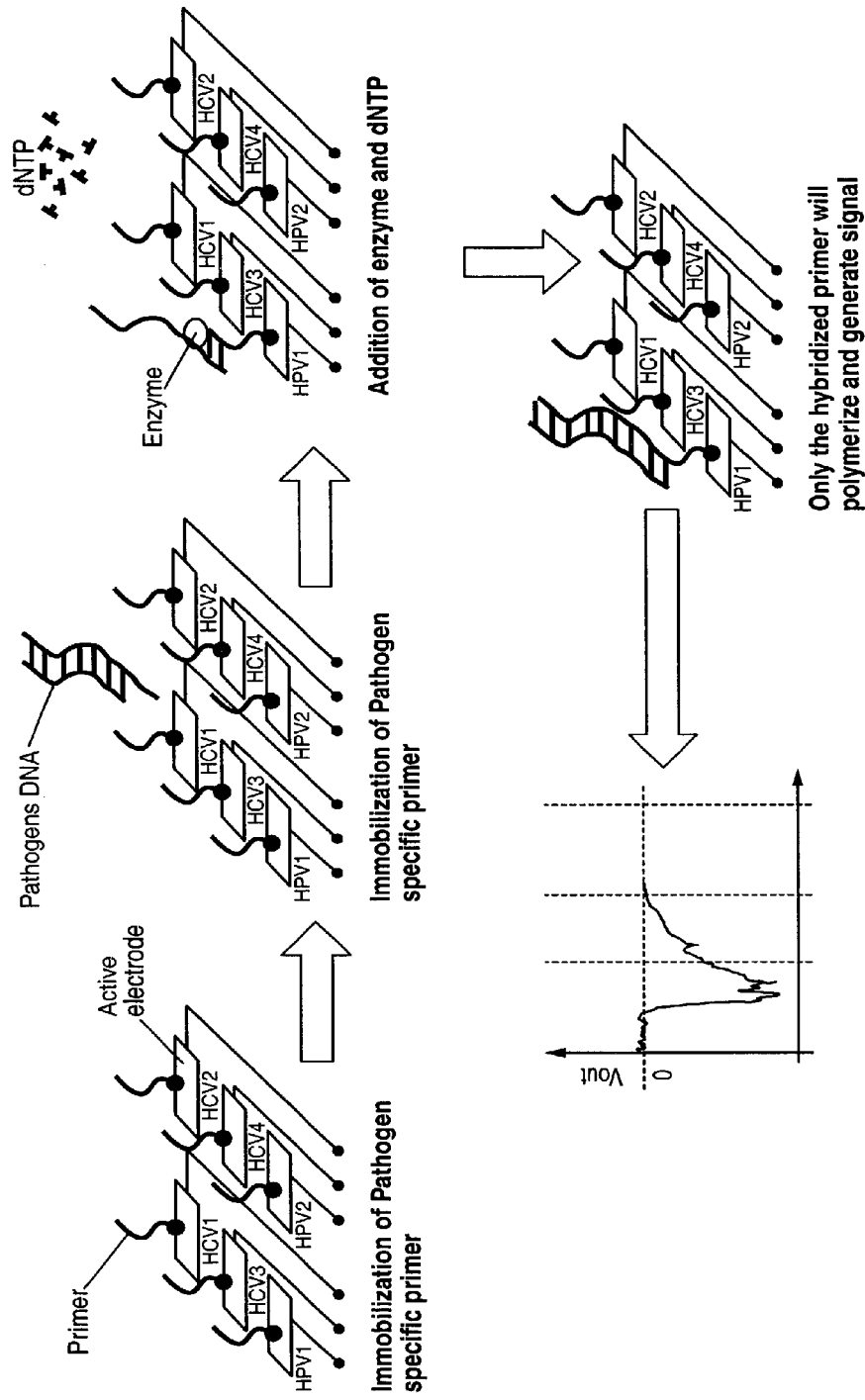
FIG. 8 schematically illustrates a microbial pathogenic detection protocol according to the subject invention.

Yet another application in which the subject methods find use is in the detection of microbial nucleic acids, e.g., nucleic acids from pathogenic microbial species, in a sample, and therefore microbial detection in a sample. This method is schematically illustrated in FIG. 8. In the protocol illustrated in FIG. 8, the first step is to provide a system having an immobilized primer for a nucleic acid found in each microbial species to be detected. A sample to be assayed, e.g., a sample from a host or patient suspected of carrying the microbial species of interest, is then prepared and contacted with the immobilized primer(s) under suitable hybridization conditions, e.g., stringent conditions, to produce a duplex structure when the microbial species of interest is present. Next, one or more dNTPs, including the dNTP that will be added to the primer if the duplex is present, are contacted with the immobilized primer. If the pathogen was present in the sample, a duplex would be formed and polymerization would occur, giving rise to a detectable transitory electrical signal. However, if the pathogen is not present in the assayed sample, no immobilized duplex would be produced and no transitory electrical signal observed.

Also coming under the above broad category of applications are gene expression profiling applications. In these applications, the presence of a plurality of expressed genes, as measured by the presence of mRNA transcripts or synthetic derivatives thereof present in amounts proportional thereto, in a sample is detected, either qualitatively or quantitatively, and usually quantitatively, to obtain an expression profile of the sample. By plurality is meant at least 2, usually at least 5, and more usually at least 10, where the number of different genes that may be assayed for expression may be much greater, e.g., about 100, about 200, about 300, about 500, about 1000, about 2000, or more, depending on the particular protocol. In the gene expression profiling applications of the subject invention, a plurality of mRNA transcripts in a sample may be detected directly, or derivatives of the subject mRNA transcripts, e.g., RNA or cDNA derivatives, such as cRNA, cDNA etc., may be detected and used to derive the gene expression profile. A variety of different expression profiling protocols are known to those of skill in the art, where the expression profile of 2 or more genes in a sample is determined by looking at mRNA transcripts directly, or cRNA, cDNA, amplified DNA etc, produced from an initial set of mRNA transcripts.

Figure 19A:
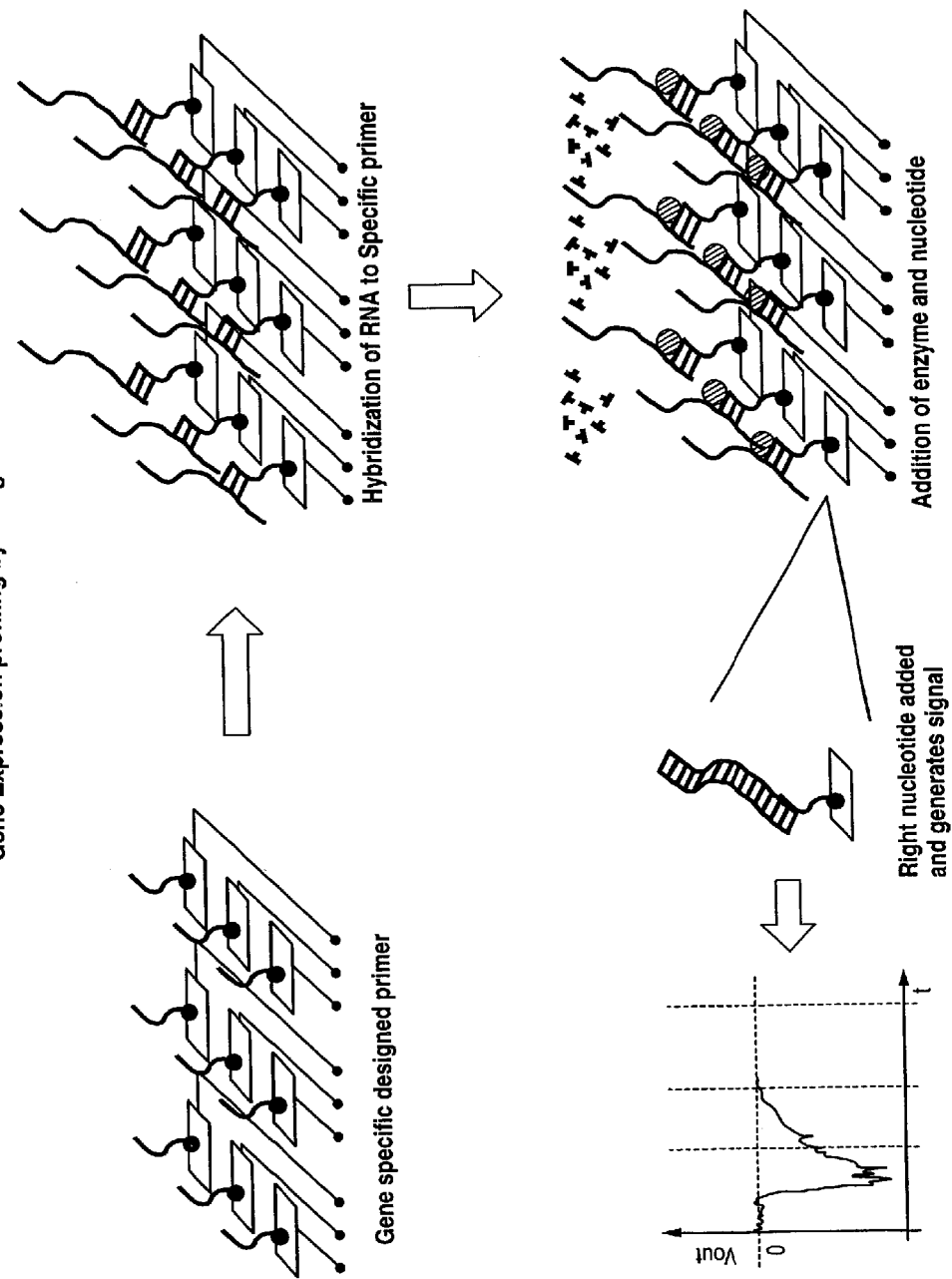

In the subject methods, an electrode detection element comprising a working electrode having a primer specific for a target mRNA (or nucleic acid derivative thereof) is contacted with a sample to be profiled, where the initial mRNA transcripts of the sample may have been processed to produce RNA or DNA derivatives thereof, as described above. For each specific gene to be assayed for expression, a different primer/electrode element is employed. Thus, where the expression of 100 different genes in a sample is to be profiled by assaying the sample for the presence of 100 different mRNA transcripts or nucleic acid derivatives thereof, 100 different electrode detection elements are employed, where each detection element at lease includes a working electrode displaying at least a primer specific for the nucleic acid of interest on its surface. Where individual electrode detection elements are employed, each different element may be sequentially contacted with sample to produce immobilized template/primer structures. Alternatively, where a combined array of individual elements is employed, e.g., as present on an array or other integrated device, each of the distinct detection elements may be contacted with the sample simultaneously. If the initial sample expresses the gene of interest, a template/primer duplex is formed on the detection element. Next, the resultant immobilized template/primer structures are contacted with reaction buffer, polymerase and dNTP, typically all four dNTPs and the sample(s) is monitored for a transitory electrical signal. In this manner, the expression of a plurality of genes in a sample is readily determined. By using arrays of electrode/primer structures, gene expression profiling in high throughput format is readily accomplished. As discussed in greater detail below, in those embodiments where arrays of detection elements are employed, each detection element is typically contacted with a fluidically isolated sample. FIGS. 19a and 19b provide schematic representations of two representative gene expression profiling protocols as described above. In addition to the above described applications, For example, total RNA/cDNA is incubated with pre-immobilized gene specific primers (probe) in an array of electrodes. These probes which are specific sequencing/extension primers with the 5'/3' end over the base of interest, provide for hybridization to the RNA/cDNA in the presence of suitable hybridization buffer. The resultant template/primer fragments are then used as substrate in a primer extension reaction in the presence of reverstranscriptase/DNA polymerase enzyme and all four deoxynucleotides. When nucleotides are added and extension occurs, the electrostatic response of a group of identical RNA/cDNA molecules creates a unique waveform from which one can identify and evaluate the mass of the molecules for gene expression profiling.

In practicing the above methods, standard polymerase mediated template dependent primer extension reaction conditions are employed. As such, in the subject methods the medium assayed for the transitory electrical signal is made to include all of the necessary components for the desired reaction to occur, which components at least include: (a) primer/template duplexes on the working electrode surface; (b) dNTP(s); (c) a quantity of reaction buffer; and (d) polymerase. The following guidelines are based on the preparation of a 50 µl Fl total volume reaction mixture. As such, the below specific amounts should be varied proportionally where different amounts of total reaction mixture are prepared, where such calculations are well within those of skill in the art. In preparing the reaction mixture, the amount of duplex structures that is present on the working electrode is typically at least about 100 molecules, usually at least about $10^7$ molecules and more usually at least about $10^9$ molecules, where the amount of duplex structures may be as great as $10^9$ molecules or greater, but typically does not exceed about $10^{11}$ molecules and usually does not exceed about $10^{11}$ molecules. The amount of polymerase that is included in the reaction mixture may vary, but typically ranges from about 1 to about 100 U, usually from about 5 to about 30 U. Also included in the reaction mixture are one or more dNTPs, e.g., a single dNTP or an amount of each of dATP, dTTP, dCTP and dGTP. The total amount of dNTPs included in the reaction mixture ranges, in many embodiments, from about 1 to 500 nmols, usually from about 30 to 50 nmols and more usually from about 35 to 40 nmols, where the relative amounts of each of the specific types of dNTPs may be the same or different. Also included in the reaction mixture is a quantity of reaction buffer, where suitable reaction buffers are known to those of skill in the art. The amount of reaction buffer used to prepare the subject reaction mixtures typically ranges from about 1 mM to about 10 mM usually from about 2 mM to about 5 mM. As mentioned above, the above amounts are provided for a 1 ml reaction, and may be adjusted to any other reaction volume. Such adjustments are well within the abilities of those of skill in the art. In preparing the reaction mixture, the various constituent components may be combined in many different orders. Following preparation of the reaction mixture, the reaction mixture is subjected to conditions sufficient for template dependent primer extension to occur. These conditions are typically characterized by maintaining the reaction mixture at a substantially constant temperature for a period of time sufficient for the reaction to occur. The temperature at which the reaction mixture is maintained during this portion of the subject methods generally ranges from about 4 to about 75, usually from about 20 to about 43 and more usually from about 25 to about 37° C. The duration of this step of the subject methods typically ranges from about 1 millisecond to about 30 min, usually from about 2 millisecond to about 2 min and more usually from about 2 millisecond to about 3 min.

An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

The above reviewed reaction conditions are merely representative of suitable conditions that may be employed in practicing the subject methods, and are provided merely for illustration purposes. As such, they are not to be considered in any way limited on the scope of the subject invention.

The above reviewed specific applications based on the detection of template dependent primer extension reactions according to the subject invention are merely representative of all of the different applications in which the subject methods find use.

Analyte Detection Applications

In addition to the detection/characterization of template dependent primer extension reactions, the subject methods also find use in analyte detection applications. In these applications, the first molecule is an analyte of interest that specifically binds to an immobilized second molecule, where the binding event between these two molecules is detected by detecting a transitory electrical signal in the medium caused by movement of the analyte first molecule towards the immobilized second molecule. Because a binding event and transient electrical signal only occurs when the analyte of interest is present in the assayed sample and does not occur when the analyte of interest is absent, monitoring of the medium for the presence of a transient electrical signal provides immediate information as to whether the sample being assayed does or does not include the analyte of interest.

In these applications, the presence of a particular analyte or analytes in a given sample is detected at least qualitatively, if not quantitatively. In analyte detection applications of the subject invention, a sample suspected of comprising the analyte(s) of interest is contacted with an electrode displaying an immobilized molecule, e.g., ligand, that specifically binds to the analyte, and the sample medium is monitored to for the signature transitory electrical signal. The sample is maintained at a suitable temperature, e.g., from about 4 to about 30, usually from about 4 to about 25° C., for a sufficient period of time, e.g., from about 1 min to about 180 min, for any binding event to occur if the analyte is present in the sample. If the analyte of interest is present in the sample, it moves towards its immobilized ligand to bind to it, and generates the transitory electrical signal. If the analyte is not present, no transitory electrical signal is generated. As such, by monitoring the sample for the presence of the transitory electrical signal, the presence of the analyte of interest in the sample is readily determined.

A variety of different analytes may be detected using the subject methods, where representative analytes of interest include, but are not limited to: polypeptide analytes, including proteins and fragments thereof; nucleic acids, including oligonucleotides and polynucleotides, both DNA and RNA; polysaccharides; hormones; toxins; and the like. Specific representative analyte detection applications of interest include, but are not limited to: antibody-antigen binding event detection applications; protein-protein interactions; ligand-receptor applications; and nucleic acid hybridization applications. Each of these representative applications is described separately below in greater detail.

Figure 9:
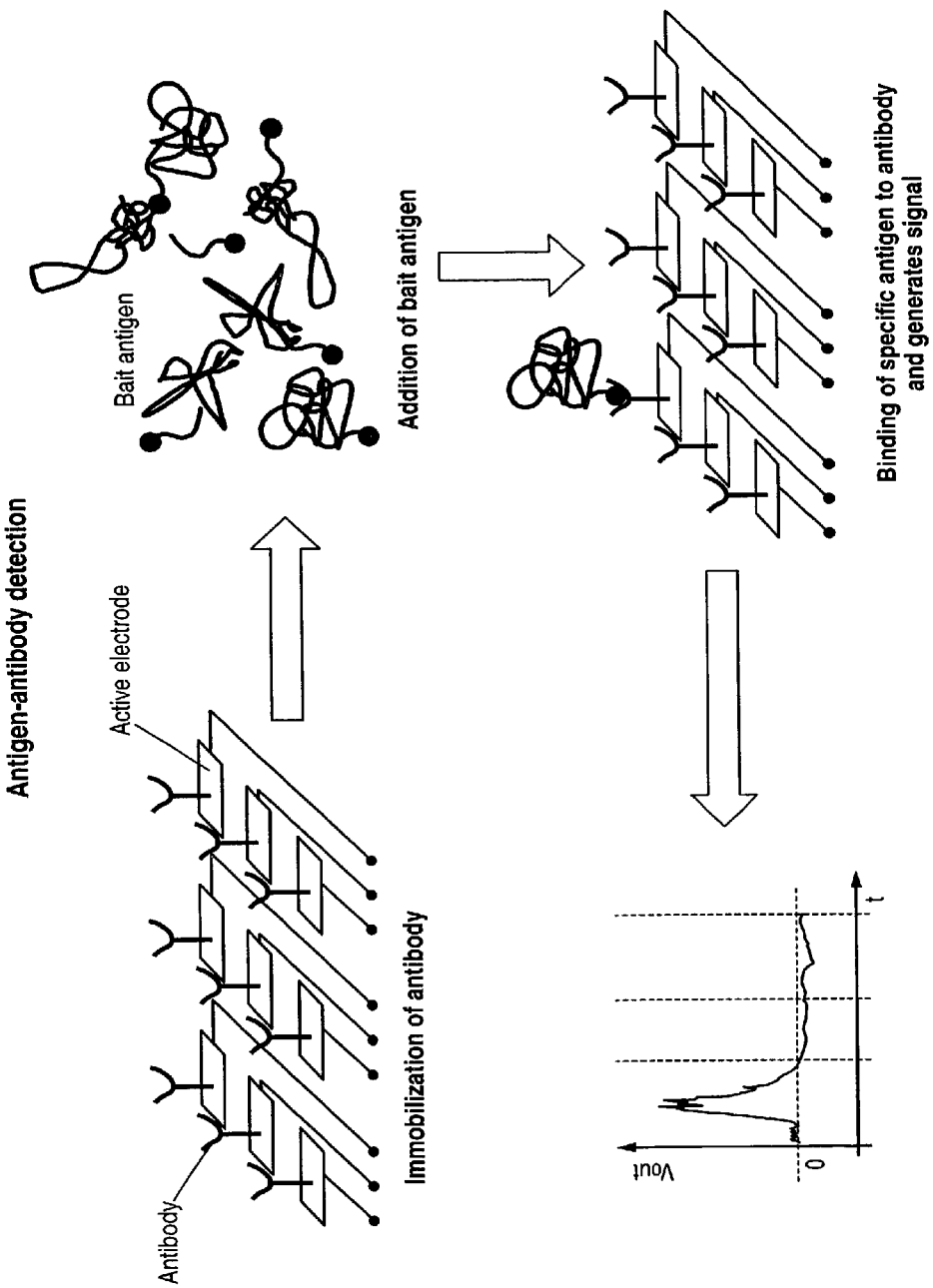
FIG. 9 provides a schematic illustration of an antibody-antigen detection application according to the subject invention.

FIG. 9 provides a schematic illustration of an antigen detection application according to the subject invention. In this representative protocol, an antibody specific for an antigen of interest, or binding fragment thereof, is immobilized on an electrode surface. The immobilized antibody is then contacted with a sample suspected of containing the antigen analyte of interest. The detection of a transient electrical signal indicates the presence of the antigen analyte of interest in the sample.

Figure 10:
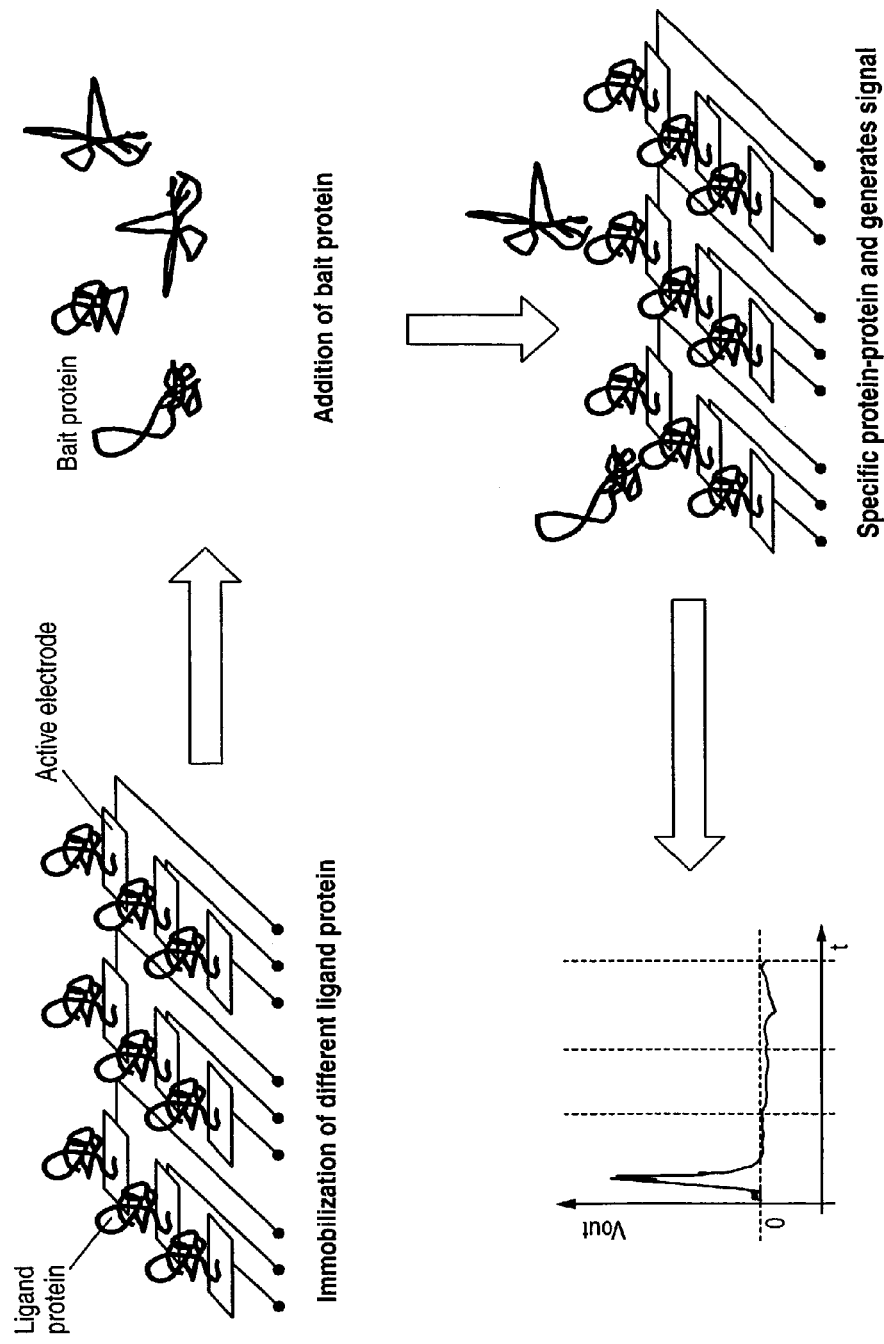
FIG. 10 provides a schematic illustration of a protein-protein interaction assay according to the subject invention.

FIG. 10 provides a schematic illustration of a protein-protein interaction assay according to the subject invention. In this application, a known protein "bait" is immobilized on the surface of the electrode. The electrode is then contacted with a sample containing known and/or unknown proteins and any resultant protein-protein interactions between the known immobilized bait protein and known or unknown prey proteins present in the sample are detected by detecting a transient electrical signal in the sample.

Figure 11:
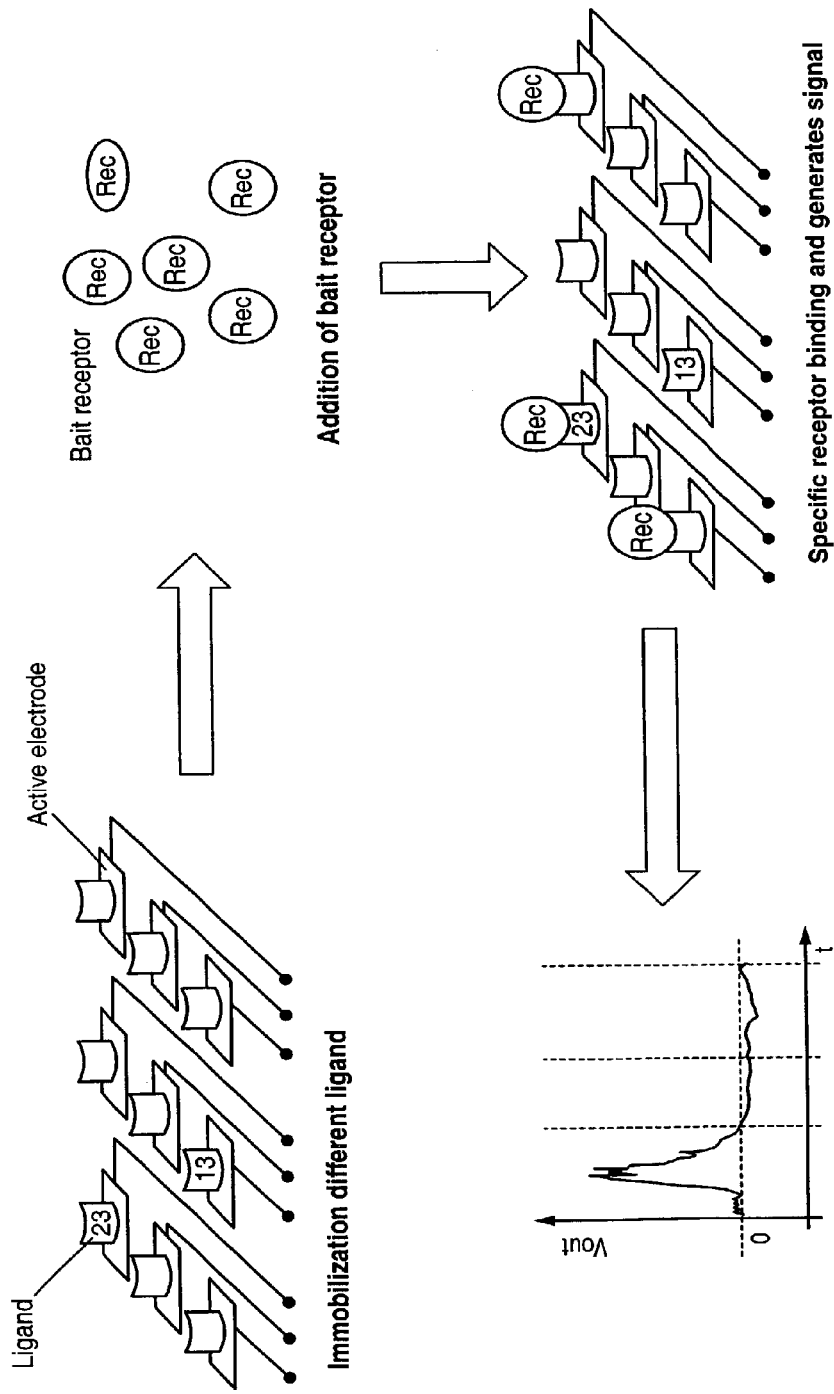
FIG. 11 provides a schematic illustration of a ligand-receptor assay according to the subject invention.

FIG. 11 provides a schematic illustration of a ligand-receptor assay protocol according to the subject invention. In the protocol illustrated in FIG. 11, ligand that specifically binds to a receptor of interest is immobilized to the surface of an electrode. Next, a sample to be assayed for the presence of receptor for the ligand is contacted with the immobilized ligand. Any resultant transitory electrical signal observed following contacted is detected and related to the presence of receptor in the assayed sample.

Figure 12:
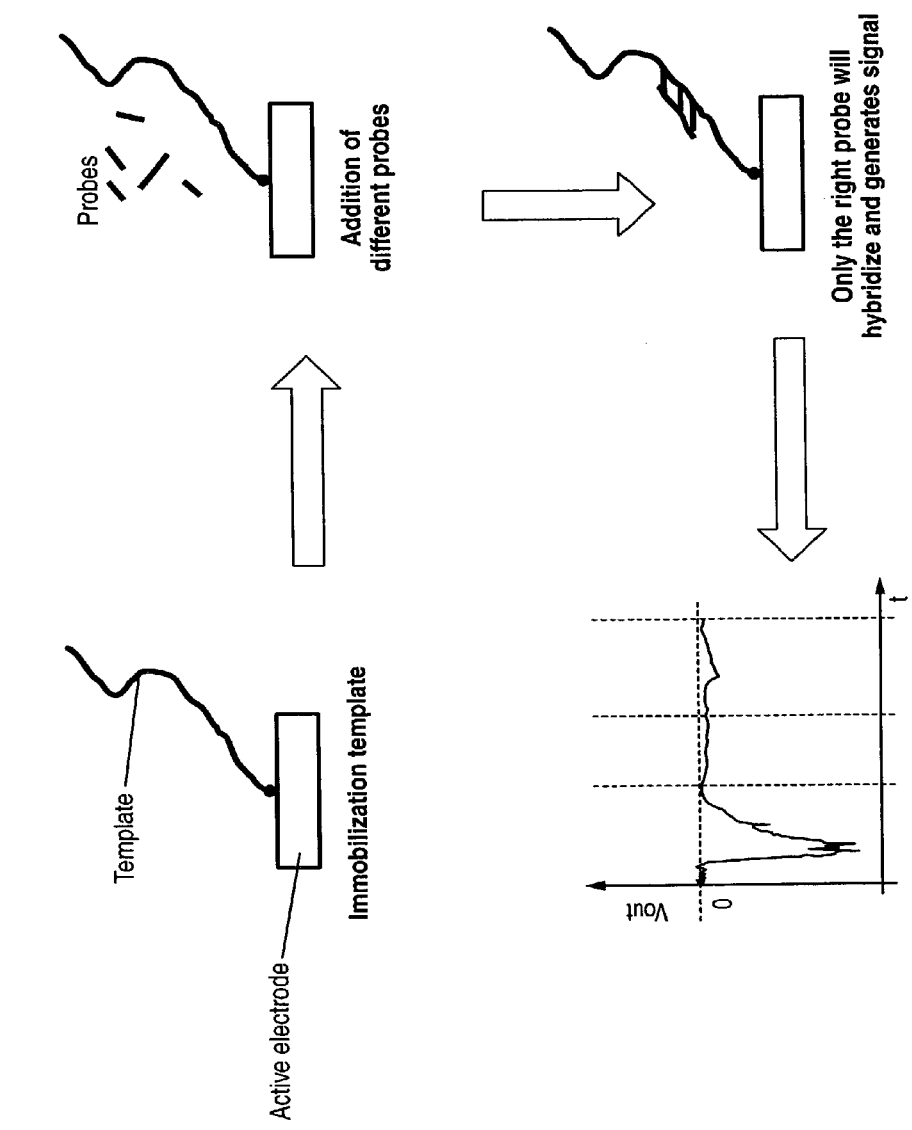
FIG. 12 provides a schematic illustration of a hybridization assay according to the subject invention.

FIG. 12 provides a schematic illustration of a hybridization assay according to the subject invention, in which the presence of a nucleic acid analyte in a sample is detected by detecting a transitory electrical signal in the sample that is generated by movement of a nucleic acid probe towards an immobilized nucleic acid target to which the probe hybridizes.

In certain embodiments, the subject analyte detection methods are performed in a high throughput format, in which a plurality (e.g., 5, 10, 25, 50, 100, 500, 1000, 10,000 or more) of analytes in a sample are assayed at the same time. In such embodiments, arrays of detection elements each made up of a specific analyte ligand immobilized on electrode surface are employed. In these embodiments, the arrays are contacted with the to be assayed sample under conditions sufficient for the analyte to bind to its respective binding pair member ligand that is present on the array. Thus, if the analyte of interest is present in the sample, it binds to the array at the site of its complementary binding member and a complex is formed on the array surface. The formation of this binding complex on the array surface is detected by monitoring a transitory electrical signal in the sample. In many of these array embodiments, each different ligand/electrode structure has its own isolated sample, so that only the transitory electrical signal arising from movement of an analyte towards a single electrode is observed. In other words, each distinct working electrode of the subject array is contacted with a fluidically isolated sample. Representative array devices of the subject invention are described in greater detail below. The presence of the analyte in the sample is then deduced from the detection of transitory electrical signal.

Specific analyte detection applications of interest that employ array device embodiments of the subject invention include hybridization assays in which the nucleic acid arrays of the subject invention are employed. In these assays, a sample of target nucleic acids is first prepared, where preparation may include isolation of mRNA transcripts from an initial source, and may also include the production of nucleic acid derivatives of such transcripts for use as target. Following sample preparation, the sample is contacted with the array under hybridization conditions, whereby complexes are formed between target nucleic acids that are complementary to probe sequences attached to the array surface. The presence of hybridized complexes is then detected by detecting transitory electrical signals in each, typically fluidically isolated, sample contacting each distinct detection element. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

Devices

Also provided by the subject invention are devices for use in practicing the above described methods. The subject devices include at least the following components: (1) an electrode detection element; and (2) an output signal processing element. Each of these elements is described separately below.

Figure 13:
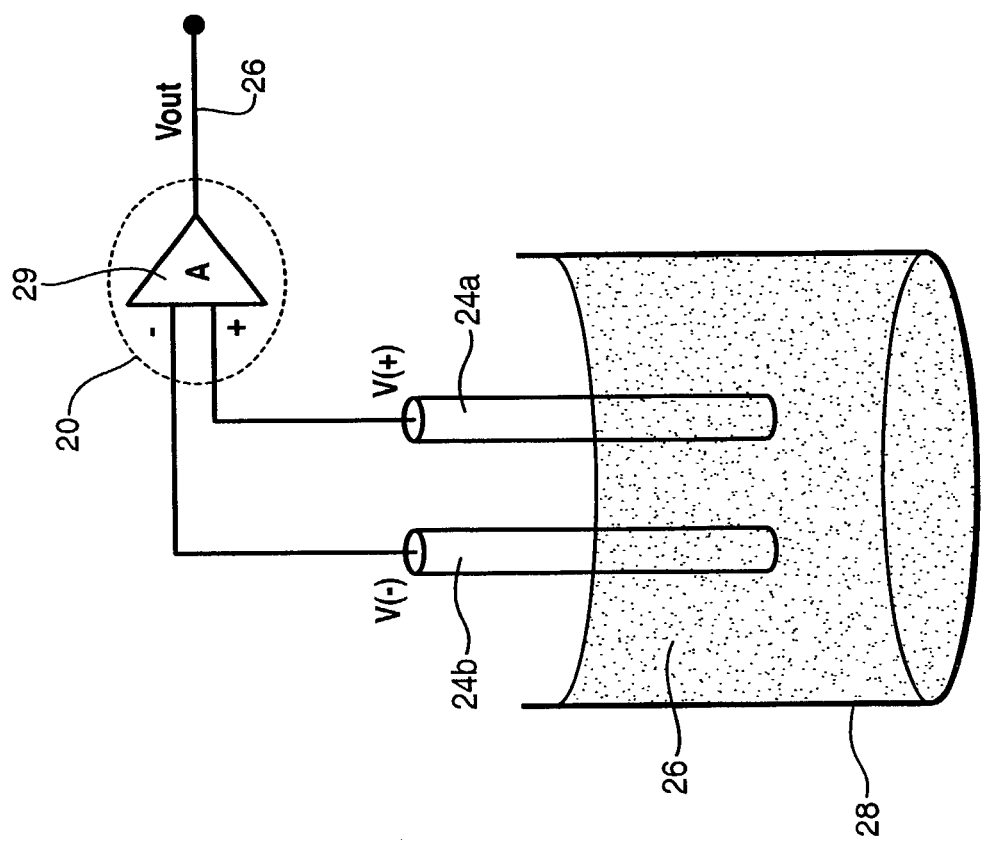
FIG. 13 provides an illustration of a representative electrode detection element according to the subject invention.

Electrode detection elements of the subject devices include at least one working electrode displaying an immobilized molecule (i.e., second molecule) on it surface. In many embodiments, the electrode detection elements include two electrodes, one of which displays an immobilized molecule (e.g., ligand, template/primer duplex, etc.) on its surface. FIG. 13 provides an illustration of a simple electrode detection element according to the subject invention. In FIG. 13, sensor device 20 includes output lead 22 and working electrode 24a and reference electrode 24b. Working electrode 24a has immobilized second molecule on its surface (not shown). Upon immersion of sensor 20 into sample 26 held in container 28, movement of analyte in the sample that specifically binds to the immobilized second molecule on working electrode 24a is detected using the electrode sensor element 20 and an output signal is generated and sent out of the sensor by output 22, e.g., to output signal processing element. Integrated into the sensor element shown in the figure is a differential amplifier 29. Although a single sensor element is shown in FIG. 13, an array of such electrode sensing elements can also be employed, e.g., for use in the high throughput assaying of a number of individual samples, e.g., as may be found in the wells of a microtitre plate, such as a 96 or 384 well plate, where the array of electrode sensing elements may include a corresponding number of individual sensing elements.

Figure 14:
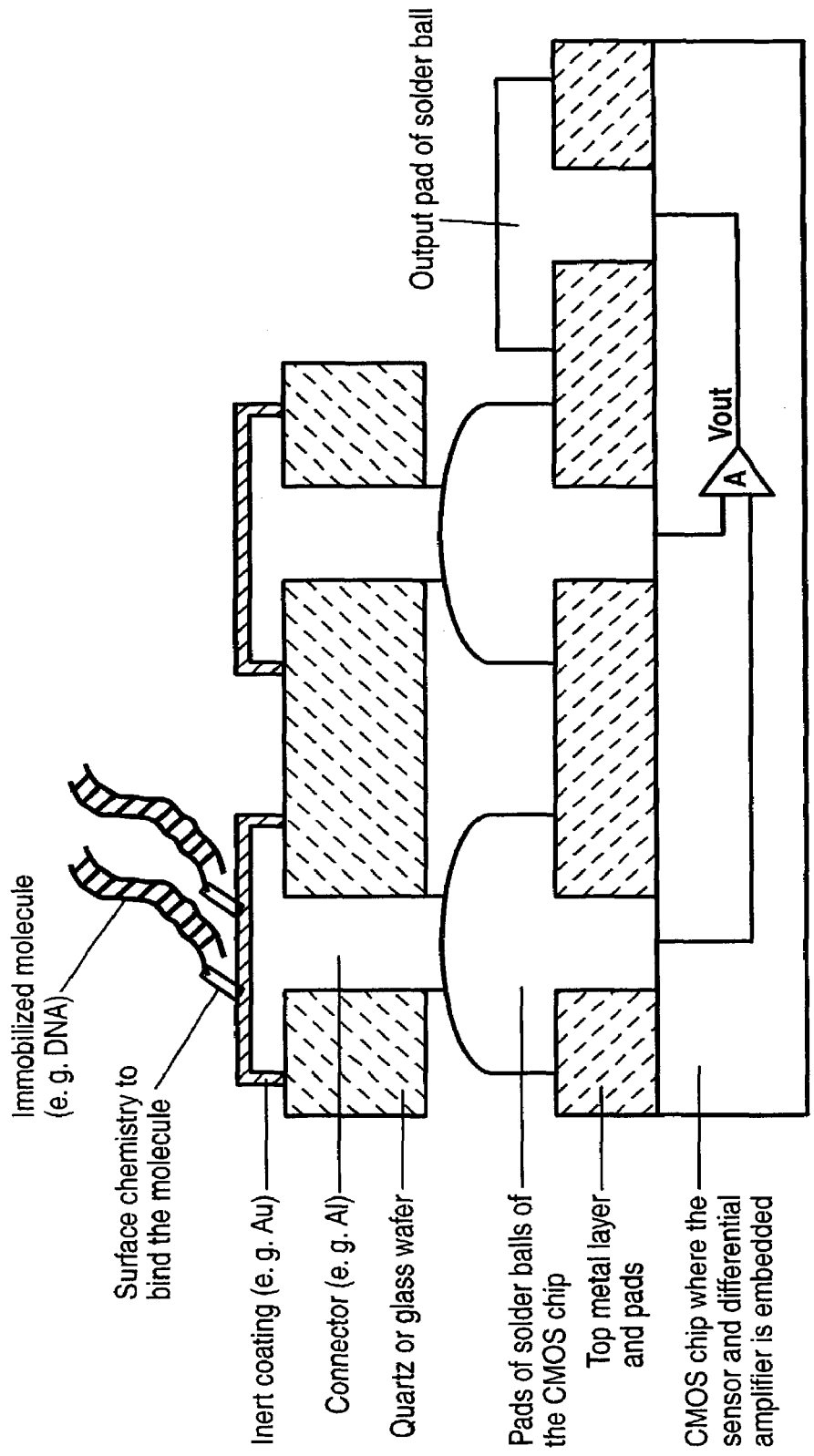
FIG. 14 provides a blow up view of an integrated silicon chip device according to the subject invention.

In yet other embodiments, the electrode sensing element is part of an integrated device that further includes a sample containment means. In many of these embodiments, the integrated device takes the form of a chip (e.g. "lab on a chip") or array structure. A portion of a representative integrated device having a chip or structure is provided in FIG. 14. In FIG. 14 a representative integrated sensor using a CMOS chip is shown. The electrode array is electrically connected via pads and/or solder balls (ball grid array packaging) to the CMOS chip. The sensors, differential amplifiers and signal routing are embedded in the CMOS chip and the output signal is available on a pad and/or solder ball. The electrode array itself can be placed on quartz, glass, or silicon oxide covered planar wafer). To build the CMOS chip one can use any commercially available CMOS process considering the necessary performance and area of each sensor, which is well within the ability of those of skill in the art. See also FIG. 22 which is further described in the Experimental Section, below.

Figure 15:
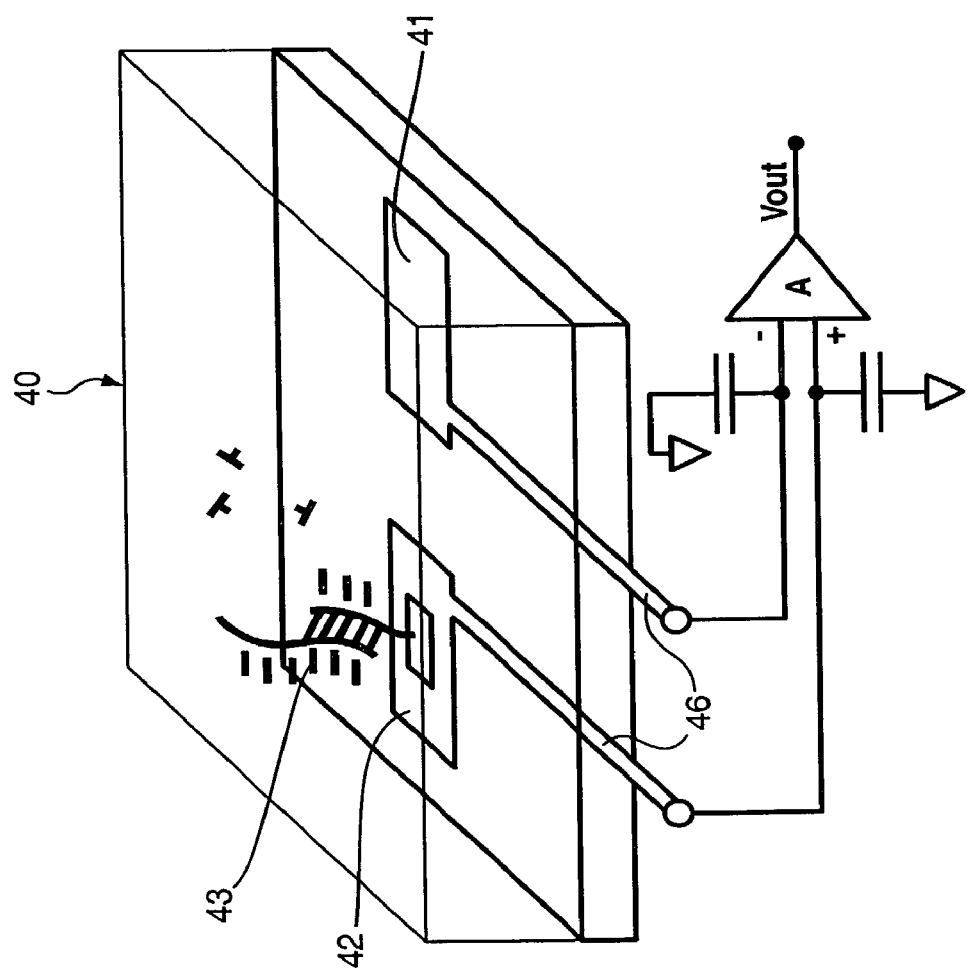
FIG. 15 provides an illustration of a device suitable for use in the detection of template dependent primer extension reactions.

An integrated array device is depicted in FIG. 15. In FIG. 15, device 40 includes glass substrate 41 on which is present a first planar electrode 42 having a primer/template duplex 43 immobilized thereon (i.e. a planar working electrode) and a second reference electrode 44. Also shown are electrode output leads 46. Electrode sensing element depicted in FIG. 15 made up of the working and reference electrode is present on an array having a plurality of such sensing elements, where each sensing element is fluidically separated from other sensing elements on the array, e.g., by low walls or other types of fluid barriers, as is well known in the microarray art. See e.g., U.S. Pat. Nos. 5,807,522 and 5,545,531 in those sections where fluidic barriers on the surface of a substrate are disclosed (the disclosures of which are herein incorporate by reference, as well as in WO 93/17126. In the electrode sensing element of FIG. 15, the working and reference electrode can be employed to observe a transient voltage generated by polymerization on the working electrode surface, which transient voltage is the transient electrical signal employed to detect the template dependent primer extension reaction.

Figure 16:
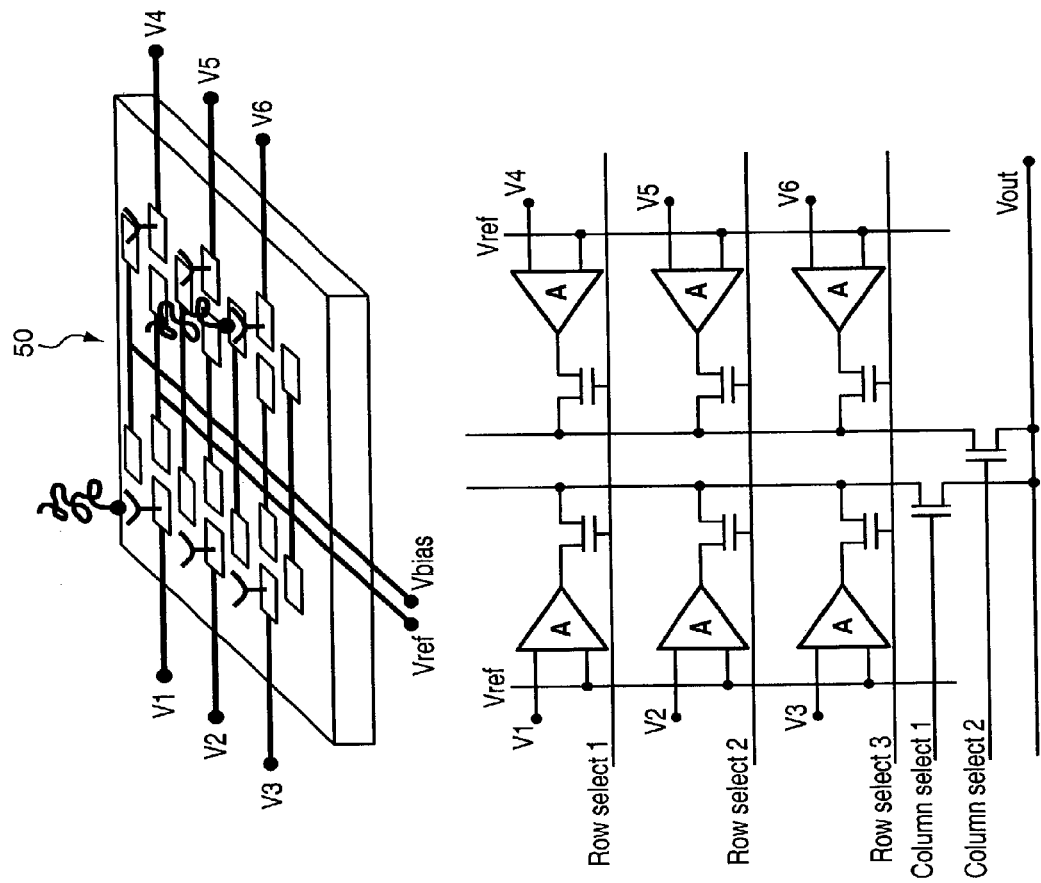
FIG. 16 provides an illustration of an array device suitable for use in high throughput proteomic screening applications.

FIG. 16 provides another embodiment of an array device according to the subject invention. In the device depicted in FIG. 16, the array includes 6 separate electrode sensing elements V1 to V6, one for each of six different receptors. Each sensing element is fluidically separated from the other sensing elements on the array surface. The sensing elements are present on a silicon substrate. Binding of a ligand to its receptor on the array surface generates a transient potential, which signal is detected using the electrode sensing element and used to determine the presence of the binding event.

Other device configurations are possible, with the above specific device embodiments being reviewed merely for representative purposes. As the above discussion demonstrates, single electrode sensing devices as well as more complex, integrate devices such as chip and array devices, are included within the scope of the invention.

In addition to the above described electrode sensing element, the subject devices typically further include a signal processing element for deriving at least one characteristic feature of the first and second molecules in the sample from the observed transitory electrical signal, i.e., for relating the output transitory electrical signal to at least one characteristic feature of the first and second molecules in the sample. This signal processing element typically includes a software component and a hardware component, where the software component is made up of an appropriate algorithm recorded on a computer or processor readable storage medium. The algorithm present on the storage medium is one that reads the observed output transitory electrical signal provided by the electrode sensing element of the device and processes it to provide information about the at least one characteristic feature of interest. The computer or processor readable storage medium on which the algorithm is stored may be any convenient medium, including CD, DAT, floppy disk, RAM, ROM, etc, which medium is capable of being read by a hardware component of the device.

The above described integrated devices can take a variety of different formats, which formats include self-contained "lab on a chips" structures which include, in addition to the sample medium containment element and electrode sensing elements described above, various flow paths, junctions, etc., reagent ports, viewing windows, etc, all included in a microfluidic device. A multitude of different microfluidic devices are well known to those of skill in the art and may be readily modified to provide integrated devices of the present invention. Representative U.S. patents that describe various microfluidic devices and the structures present therein include, but are not limited to, U.S. Pat. Nos. 6,300,141; 6,287,850; 6,271,021; 6,251,343; 6,235,175; 6,213,151; 6,171,850; 6,123,819; 6,103,199; 6,054,277; and 5,976,336; the disclosures of which are incorporated herein in their entirety.

Systems

Also provided by the subject invention are systems for use in practicing the subject method methods. The subject systems include a device, as described above, and a conducting medium, e.g., a gel, gaseous or fluid conducting medium. In addition, the subject systems may include any reagents required for practicing the subject methods, e.g., buffer solutions, nucleotides, enzymes (such as klenow) and the like.

The following examples are offered by way of illustration and not by way of limitation.

EXPERIMENTAL

I. DNA Sequencing Application

A. Materials and Methods

1. Synthesis and Purification of Oligonucleotides

The oligonucleotides BMPUP (5'-BIOTIN-CGGC-GATAAAGGCTATAACGG)(SEQ ID No. 01) and MPB-DOWN (5'-GTGGAACGCTTTGTCCGGGG) (SEQ ID No. 02) were all synthesized and HPLC purified by MWG Biotech (High Points, N.C., USA).

2. In vitro Amplification and Template Preparation

PCR reaction was performed using BMPUP and MBP-DOWN for amplification of the multi-cloning site of the vector pMBP. The biotinylated PCR products were immobilized onto streptavidin coated super paramagnetic beads (Dynabeads M280 Streptavidin Dynal A. S., Oslo, Norway).

Single-stranded DNA was obtained by removing the supernatant after incubation of the immobilized PCR product in 0.10 M NaOH for 3 minutes. Sequencing primers were hybridized to the immobilized ss-DNA strand in 10 mM Tris-acetate pH 7.5, and 20 mM magnesium acetate.

3. Electrodes

Two gold coated electrodes are used in the experiment. One of the electrodes is made of iron (a magnetic material) and the other is made of copper.

4. Sensor Description

The sensor for measuring the net static charge of the immobilized DNA ions is a simple differential voltage amplifier. This amplifier was built using the chopper-stabilized operational amplifier TLC2652A (in case large gains were required) in a negative feedback configuration.

5. Charge Sequencing

Figure 17A:
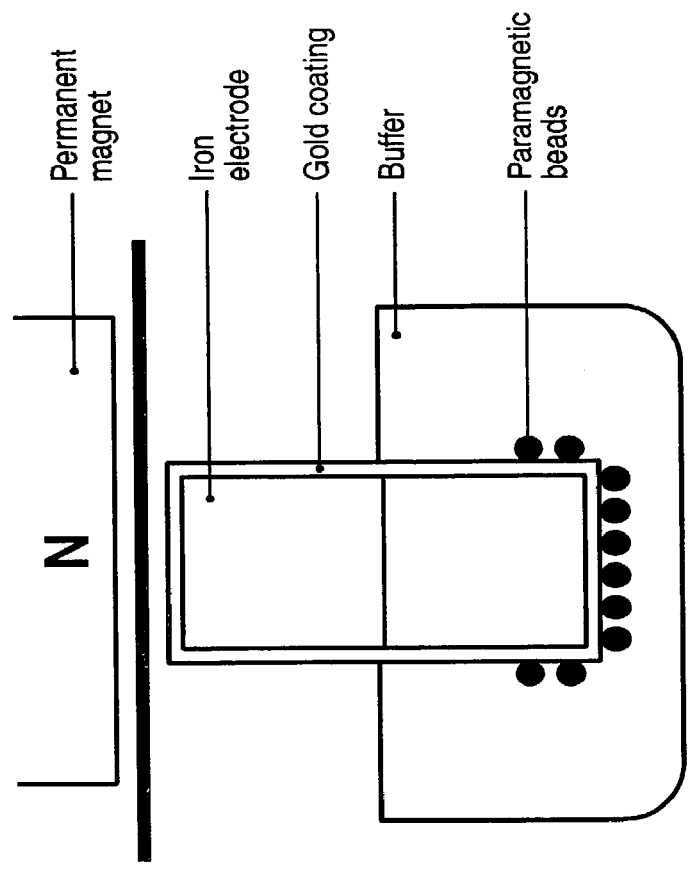
FIGS. 17A and 17B provide illustrations of a prototype device employed in Example 1 of the Experimental Section, below.

First, in order to immobilize DNA ions, the iron electrode was dipped in a primed and immobilized PCR solution. A permanent magnet is placed on top of the iron electrode to create a magnetic field to attract paramagnetic beads which carry the DNA ions (FIG. 17A). Once the beads stick to the surface of the electrode (this takes a few seconds), DNA ions become electrically connected to the electrode.

Next, the iron electrode is taken out of the PCR solution and placed in the reaction buffer (0.1 M tris-acetate (pH 7.75), 0.5 mM EDTA, 5 mM magnesium acetate, 0.1% BSA, 1 MM dithrithreitol) at room temperature. If nucleotides are added to the reaction buffer, polymerase will incorporate the right nucleotide to the immobilized DNA ions on the electrode, which results in (partially) deionization of the immobilized DNA ions. This results in a static charge variation (namely the charge sequencing signal) on the electrode. The charge sequencing signal contains the genetic code information of the target DNA.

Figure 17B:
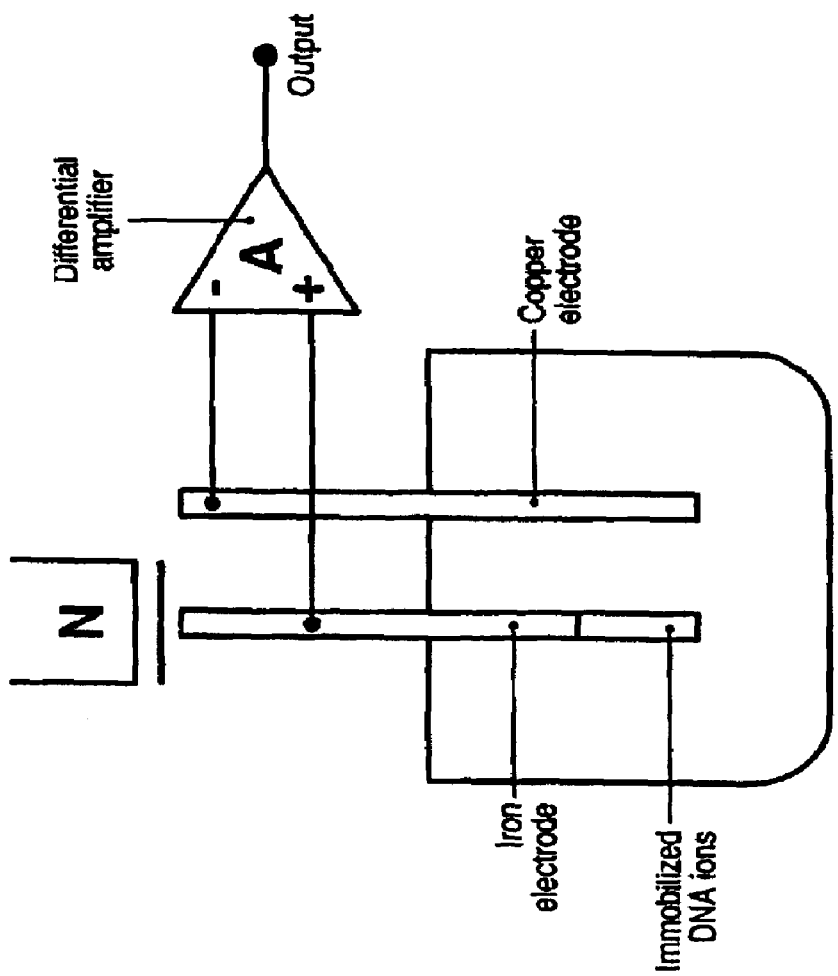
Figure 18A:
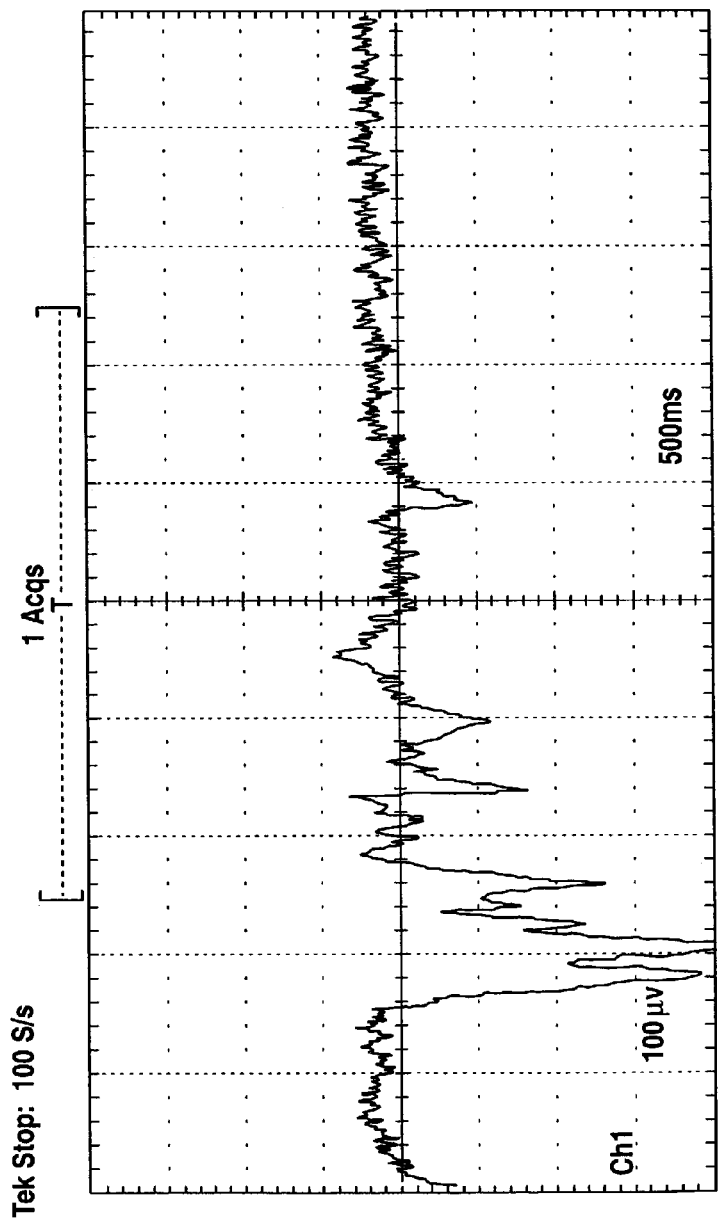
Figure 18C:
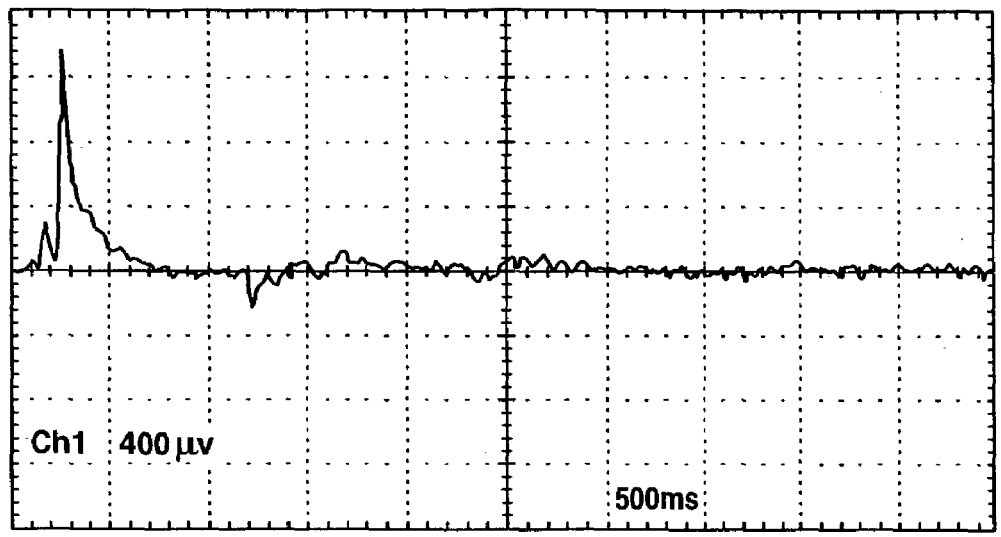
Figure 18D:
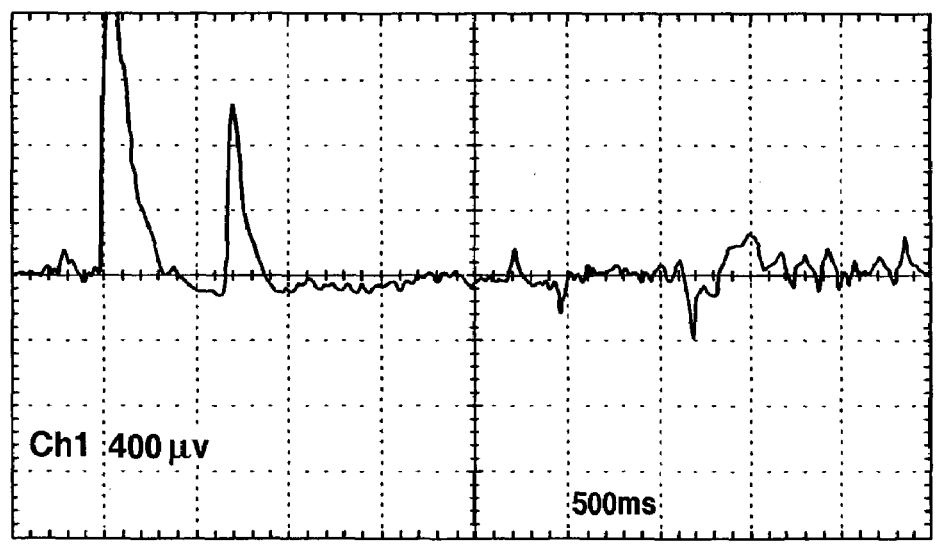
Figure 18E:
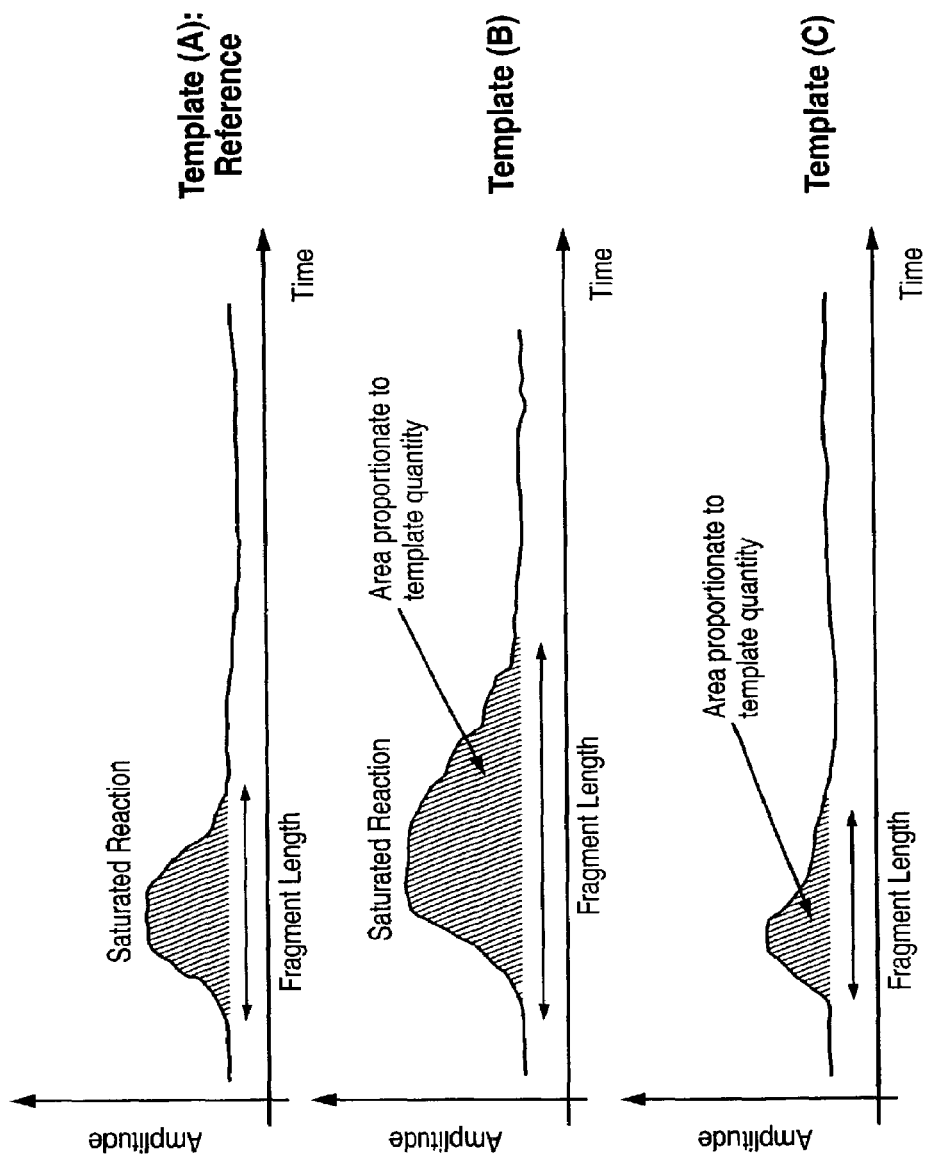

Unfortunately, the charge sequencing signal is small compared to the various noises of the system, and therefore cannot be easily recovered. For this reason, a second electrode (from gold coated copper) is placed in the reaction buffer. This second electrode is used to pick up the common mode noise in the system (i.e. common voltage of electrodes in buffer, background noise, etc.) which is then subtracted from the signal coming from the iron electrode to give a noise free charge sequencing signal for reading the genetic code. See FIG. 17B.

B. Preliminary Results

Figure 20:
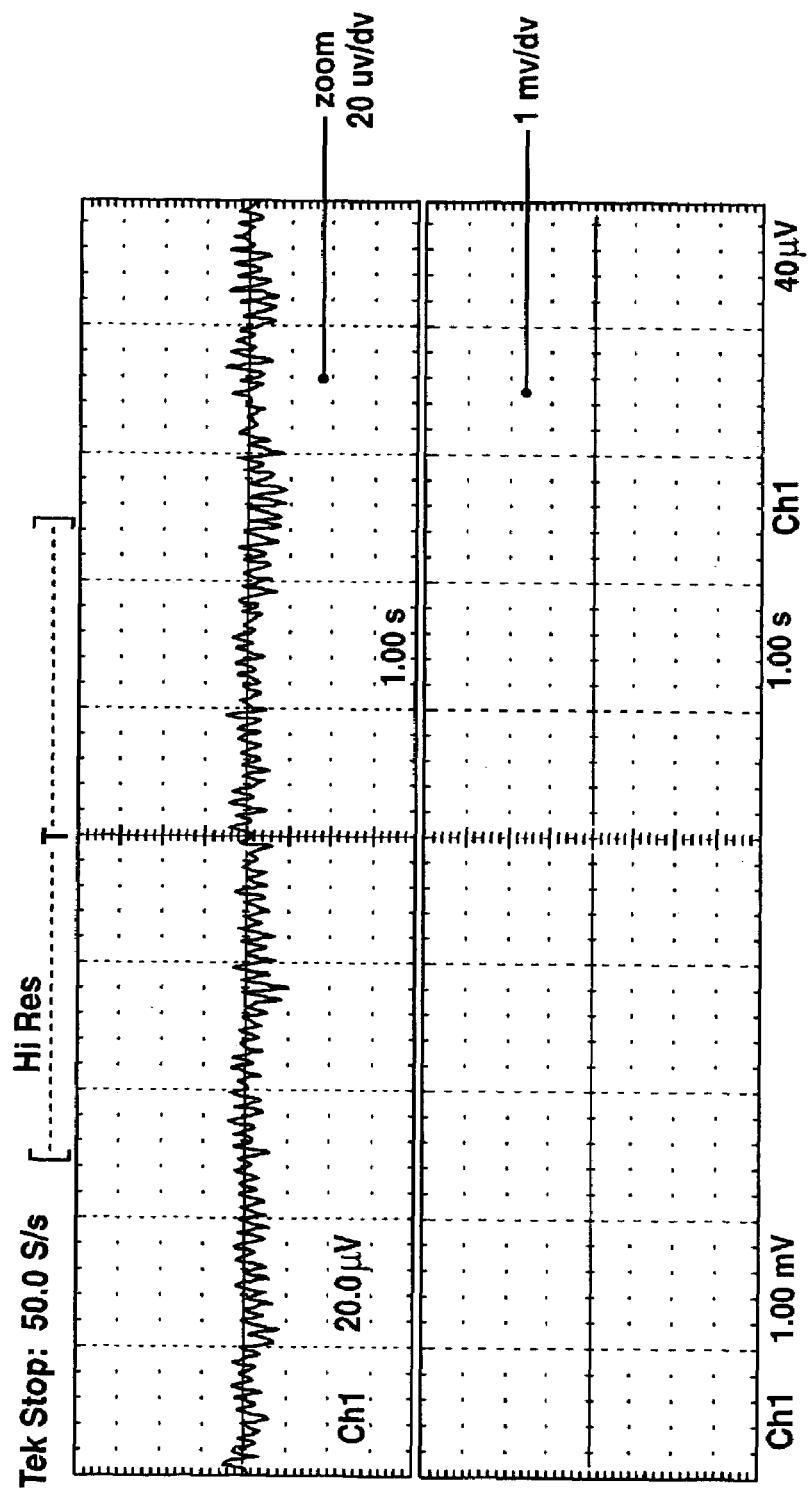
FIG. 20 provides a reading showing the noise component of an assay system according to the subject invention.

1. Background Noise: When we dipped both electrodes in the buffer the background noise of the buffer plus the noise of the amplifier was seen on the oscilloscope. We should note that it took a while (about 10 seconds) to get a stabilized background noise signal (FIG. 20). The reason was that the DNA molecules on the electrode were ionizing, and this procedure generated some net static charge on the iron electrode.

2. Single Nucleotide Added: In this case, only one nucleotide was added (which was known that it would incorporate to the DNA), and an electric pulse was observed. This signal (output of the differential amplifier) lasts for a while (3 milliseconds), and finishes when there is no site left for incorporation.

Figure 21:
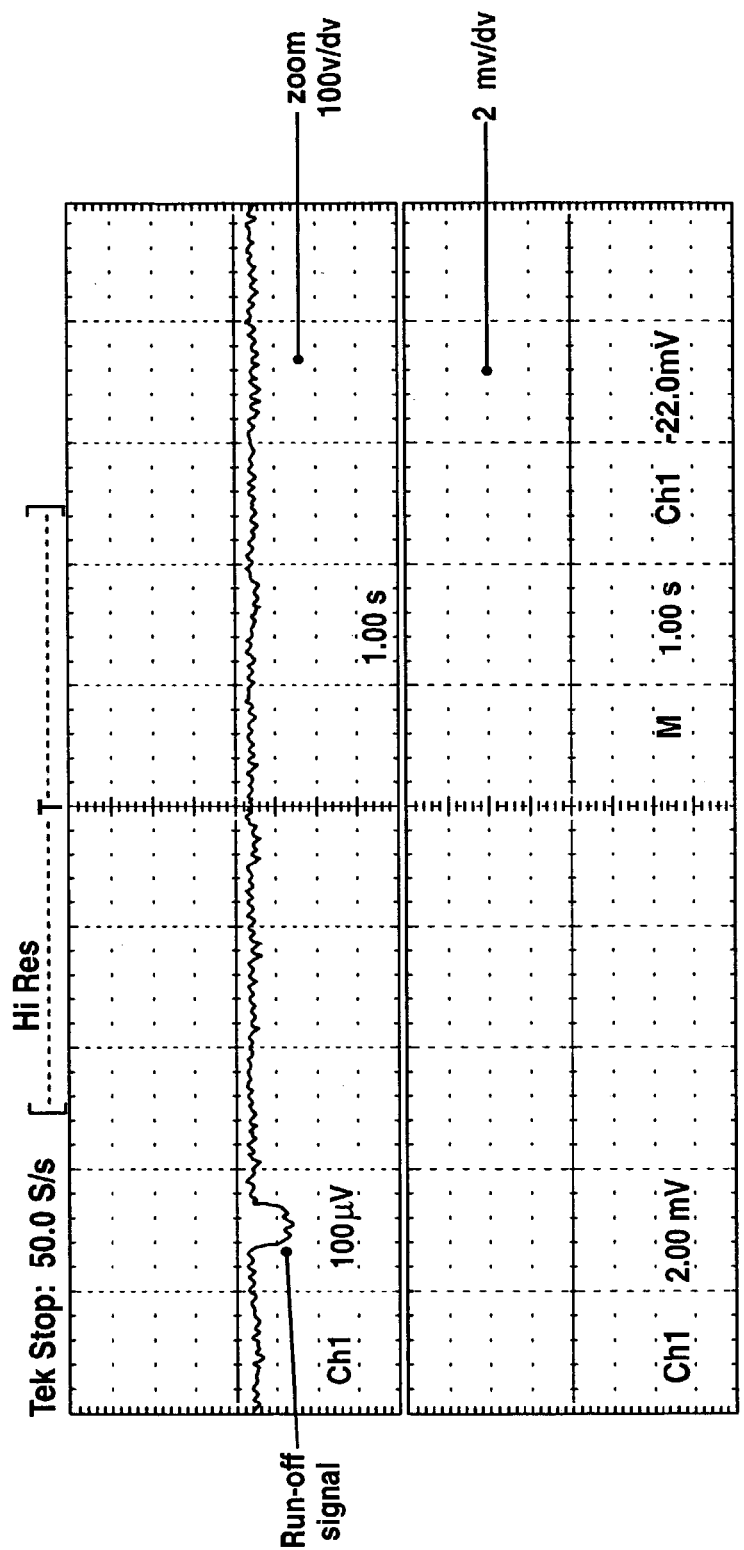

3. Run-off mode: In this case, we added all four nucleotides to the buffer. As expected, a series of electric pulses were created (FIG. 21). All of the incorporations took place in less than 1 second (400 ms). This is justified theoretically, because the amount of time needed for nucleotide incorporation is a couple of milliseconds, and in this case we had a DNA molecule with around 300 base pairs.

II. Sample Charge-sequencing Extension Signatures for 300 bp DNA Fragments.

In a charge detection method, allele-specific primer/probes are immobilized on an electrode or conductive surface and incubated with cDNA to perform analyses. Subsequent to careful washing, the electrode with immobilized ssDNA template-primer is placed in a solution containing DNA polymerase. When dNTPs are added and extension occurs, the electrostatic response of a group of identical DNA molecules creates a unique waveform (signature) from which one can quantify/evaluate the number of DNA molecules.

Figure 22:
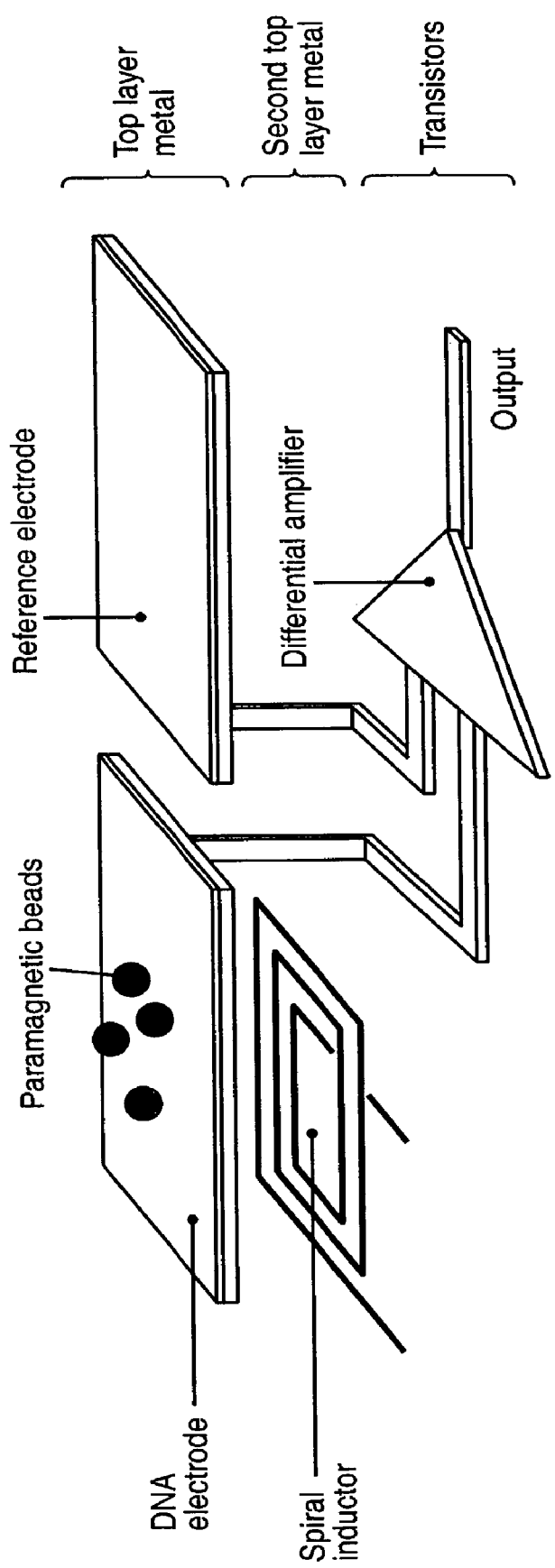
FIG. 22 provides yet another representative schematic illustration of a CMOS device according to the subject invention.

This chemistry is relatively simple because only one enzyme is used in the solution, and concept of the sensor that measures the net charge variation is relatively simple. The sensor can also be built in standard CMOS technology, which makes the platform extremely suitable to design an array of sensors on a semiconductor chip, and increase the throughput with minimum cost. See e.g., FIG. 22. In FIG. 22, the sensor (differential amplifier) can easily be fabricated on silicon (CMOS technology). The permanent magnet for immobilization can be made out of on-chip spiral inductors. With this platform one can create a single small silicon chip to sequence many samples. To move the samples to the right sensor, controllable horizontal electric fields may be employed to move DNA ions. Alternatively, the samples may be positioned on precisely on the right spot.

This method of detection is also real time because the charge perturbation of the immobilized DNA ion, which is used for reading the genetic code, occurs almost instantaneously once the electrode is placed in the solution containing polymerase and nucleotides.

The other advantages of this technology is its ability to apply current advancements of electrical engineering both in platform design which is totally electrical and on-chip, and also in pattern recognition which is common problem in communications. The speed of reaction is relatively slower than today's data acquisition systems (milliseconds, compared to nanoseconds), and there are many statistical signal processing method to interpret the signal, and extract information. A prototype of the subject invention was built in Stanford Center for Integrated Systems and tested in Stanford Genome Technology Center, and showed that the signal created by polymerization is high enough, and can easily be acquired by commercial electronic components. The experiments showed that without any extensive optimization the sensitivity of the prototype is the same as optical detection system for any application. This means that charge-sequencing platforms are a good candidate for genomic level samples.

Examples of actually observed charge sequencing expression signatures are provided in FIGS. 18A to 18E.

III. Different Representative Applications for Charge-based Detection System

A. Sample Preparation

1. RNA Extraction

RNA Extraction is performed using a commercially available RNA isolation Kit that is designed for easy, reliable, and rapid isolation of total RNA from small amounts of cells such as needle biopsy, sorted cells, micro-dissected tissue, blood or cell lines which can be obtained by using different commercially available total RNA isolation kits provided by, Ambion, Qiagen, Promega etc., etc. These systems combine a spin column with a one or two-step RNA extraction and binding method. The methods make ready-to-use RNA usually in less than 1 hour. The kit efficiently recovers high-quality total RNA for any subsequent analysis of gene expression. Method Principle: By adding RNA Extraction Buffer to the sample to extract RNA from cells. RNA is purified by spin columns and pure RNA is eluted into small volumes, usually 5-10 µl, for convenient downstream manipulations. Cell Sample: Collect cells by gentle centrifugation (2000 rpm on most centrifuges or about 400 g) for 5 minutes and remove the supernatant completely. Add 200 µl of RNA Extraction Buffer to the cell pellet. Lightly vortex to resuspend the pellet.

Tissue Sample: Add 200 µl of RNA Extraction Buffer to the tissue sample. Grind the tissue using a homogenizer such as glass-teflon or Polytron devices in the RNA Extraction Buffer. Incubate the tube on ice for 20 minutes. Lightly vortex the tube briefly every 10 minutes. Add 1 volume (200 ml) of 95-100% Ethanol to the tube. Mix briefly. Incubate the tube on ice for 10 minutes. Transfer the mixture to a spin column and place the column into a 2 ml Collection Tube. Spin the column and tube at full speed in a microcentrifuge for 1 minute. Add 200 µl of RNA Wash Buffer to the spin column and centrifuge at full speed for 1 minute to wash. Add another 200 µl RNA Wash Buffer and repeat the microcentrifuge step as above.

Transfer the column to a new 1.5 ml tube. Add 10-20 µl of RNA Elution Buffer directly to the membrane of spin column. Wait for 2 minute. Spin briefly to elute RNA. The eluted RNA now can be used immediately for any purpose or stored at −70° C. for future use.

2. Making cDNA and Immobilization

The sequences for certain genes can be retrieved from GeneBank (blast@ncbi.nlm.nih.gov). Total RNA can be prepared according to the supplier's instruction (for example, Ambion, Qiagen, Promega etc.) from peripheral blood, tissues or cell lines. First DNA strand synthesis can be obtained by using SuperScript™ pre-amplification system (Life Technologies). First strand cDNA synthesis employs a RNA/primer mixture containing, RNA and Oligo (dt) random primer or gene specific primer. These cDNAs are incubated with pre-synthesized gene specific primers which have already been immobilized on electrodes for hybridization in the presence of 20 mM Tris-HCl (pH 7.5), 8 mM $MgCl_2$ or any other hybridization buffer for later analysis.

3. Immobilization of Total RNA

Pre-synthesized gene specific primers (probe) are immobilized onto the electrodes by using different immobilization techniques. The extracted total RNA incubates with these probes for hybridization in the presence of 20 mM Tris-HCl (pH 7.5), 8 mM $MgCl_2$ or any other hybridization buffers for later analysis.

B. Sequencing

Single stranded DNA (ssDNA) is incubated with pre-immobilized gene specific primers (probe) on the surface of an electrode. These probes, which are specific sequencing/extension primer with the 3' end over the base or area of interest, provide for hybridization DNA to the ssDNA in the presence of suitable hybridization buffer. The resultant immobilized template/primer duplexes are then used as substrate in a primer extension reaction by contacting the immobilized duplex with DNA polymerase enzyme and all four deoxynucleotides, i.e., ATP, GTP, CTP and TTP. See FIG. 3. When nucleotides are added and extension occurs, the electrostatic response of a group of identical DNA molecules creates a unique waveform for each nucleotide incorporated by the polymerase from which one can identify the pattern for each incorporated dNTP. See e.g., FIGS. 18A to E and 21.

C. SNP Detection by Using Total RNA

Total RNA is incubated with pre-immobilized gene specific primers (probe) on two identical electrodes. These probes, which are specific sequencing/extension primer probes with the 5' end over the base of interest, provide for hybridization to the RNA in the presence of suitable hybridization buffer. The resultant template/primer nucleic acid duplexes or fragments are then used as substrate in a primer extension reaction with reverse transcriptase enzyme and specific deoxynucleotide which, if the template is the SNP of interest, will be covalently bonded to the 3' end of the primer nucleic acid. When nucleotides are added and extension occurs, the electrostatic response of a group of identical RNA molecules creates a unique waveform from which one can identify the pattern for SNP. See e.g., FIG. 4.1.

D. SNP Detection by Using cDNA

Synthesized cDNA is incubated with gene specific primers (probe) pre-immobilized on the surface of two identical electrodes. These probes, which are specific sequencing/extension primers with the 3' end over the base of interest, provide for hybridization to the single stranded cDNA in the presence of 20 mM Tris-HCl (pH 7.5), 8 mM $MgCl_2$ or any other hybridization buffer. The resultant template/primer nucleic acid duplexes or fragments are then used as a substrate in a primer extension reaction with polymerase and the specific deoxynucleotide that will be incorporated if the SNP of interest is present. When nucleotides are added and extension occurs, the electrostatic response of a group of identical DNA molecules creates a unique waveform from which one can identify the pattern for SNP. See e.g., FIG. 4.2.

E. SNP Detection by Using Allele Specific Primer

A set of possible combinations of allele specific primers are pre-immobilized (probe) onto identical electrodes. These probes, which are specific sequencing/extension primers with the 3' or 5' end over the base of interest, are designed to hybridize to the DNA/RNA of interest in the presence of suitable hybridization buffer. The resultant perfect match template/primer duplex nucleic acids or fragments are then used as substrates in a primer extension reaction by contacting with enzyme and deoxynucleotides. When nucleotides are added and extension occurs, the electrostatic response of a group of identical DNA/RNA molecules creates a unique waveform from which one can identify the pattern for SNP. See e.g., FIG. 4.3.

F. SNP Detection by Using PCR Product

Pre-biotinylated PCR products are immobilized onto streptavidin-coated super paramagnetic beads Dynabeads™ M280-Streptavidin (Dynal A. S., Oslo, Norway). Single-stranded DNA fragments are obtained by taking the resultant supernatant after incubation of the immobilized PCR product in 95° C. for 3 min in $H_2O$. A specific sequencing/extension primer with the 3' end over the base of interest is added and allowed to hybridize to the single stranded DNA in the presence of 20 mM Tris-HCl (pH 7.5), 8 mM $MgCl_2$ or any other hybridization buffer. The primed single stranded DNA is divided into two aliquots and immobilized onto two different electrodes. The resultant template/primer duplex nucleic acids or fragments are then used as substrate in a primer extension reaction by contact with a polymerase and specific deoxynucleotide. When nucleotides are added and extension occurs, the electrostatic response of a group of identical DNA molecules creates a unique waveform from which one can identify the pattern for SNP. See e.g., FIG. 5.

G. SNP Detection by Using Exonuclease/Degrading Enzyme

The detection of a polymorphic nucleotide present in a target nucleic acid sequence is achieved by first hybridizing to the target sequence a short oligonucleotide, i.e., a probe, which is immobilized to electrodes, such that the 3' or 5' end of the probe terminates at least one nucleotide before the polymorphic nucleotide of target. Then, using an extension reaction under appropriate conditions a Nuclease Resistant Nucleotide (NRN), like thiophosphate-modified nucleotides (2'-deoxynucleoside 5'-alpha [P-thio]triphosphates) dNTP$^S$ or boranophosphatase (2'-deoxynucleoside 5'-alpha-[P-borano-]triphosphates), is incorporated to the 3' or 5' end of the probe corresponding to the polymeric position of the target. After completion of the extention reaction the hybrid molecule is digested with an exonuclease enzyme under appropriate conditions. Probe molecules with the NRN incorporated at their 3' or 5' ends are resistant to nuclease activity, while molecules without a NRN incorporated at their 3' or 5' end are not resistant to nuclease activity and are subject to digestion. When digestion occurs, the electrostatic response of a group of identical DNA/RNA molecules creates a unique waveform from which one can identify the pattern for SNP. See e.g., FIG. 6.

H. Real Time PCR

The quantification of amplified target in a polymerase chain reaction (PCR) is achieved by first immobilizing one of the two primers onto the electrode. The resultant structure is contacted with template, the other primer, enzyme and all four dNTPs. When nucleotides are added and extension occurs, the electrostatic response in each cycle creates a unique waveform which one can evaluate/estimate the mass of the molecules for each cycle. See e.g., FIG. 7.

I. Pathogen Typing

Total RNA/DNA or amplified nucleic acids thereof of pathogen to be assayed are incubated with pre-immobilized pathogen specific primers (probe) present on an array of electrodes. These probes, which are specific sequencing/extension primers with their 3' or 5' ends over the base of interest, can hybridize to the DNA/RNA of the pathogen, if present, in the presence of suitable hybridization buffer. The resultant template/primer nucleic acid duplexes or fragments are then used as substrate in a primer extension reaction by contacting with an appropriate polymerase/reverstranscriptase enzyme and all four deoxynucleotides. When nucleotides are added and extension occurs, the electrostatic response of a group of identical DNA/RNA molecules creates a unique waveform from certain spot which one can identify and evaluate the presence of the pathogen. See e.g., FIG. 8.

J. Antigen-antibody Detection

A set of mono or polyclonal antibodies are pre-immobilized onto the surfaces of identical electrodes. These antibodies, which have affinity to certain antigens, are then incubated with different antigens in a fluidic environment in the presence of suitable buffer. When a specific interaction between the antigen and antibody occurs, the electrostatic response of a group of identical antigen/antibody molecules creates a unique waveform from which one can identify the pattern for antigen/antibody interaction. See e.g., FIG. 9.

K. Protein-protein Interaction

A set of tagged proteins is pre-immobilized onto the surfaces of identical electrodes. These tagged proteins, which have affinity to certain proteins, are then incubated with different proteins in a fluidic environment in the presence of suitable buffer. When a specific interaction between the proteins occurs, the electrostatic response of a group of identical protein-protein molecules creates a unique waveform from which one can identify the pattern for protein-protein interaction. See e.g., FIG. 10.

L. Ligand and Receptor Detection

A set of tagged ligands or receptors are pre-immobilized onto the surfaces of identical electrodes. These tagged ligands or receptors, which have high affinity to certain ligands or receptors, are incubated with different ligands or receptors in a fluidic environment in the presence of suitable buffer. When a specific interaction between the ligands or receptors occurs, the electrostatic response of a group of identical ligand and receptor molecules creates a unique waveform from which one can identify the pattern for ligand and receptor interaction. See e.g., FIG. 11.

M. Hybridization ssDNA is immobilized onto the surface of an electrode and by trial and error exposed to a set of short oligonucleotide probes. When a specific hybridization occurs, the binding interaction creates a unique waveform for each probe from which one can identify the complementary probe. See e.g., FIG. 12.

N. Gene Expression Profiling by Using Total RNA or cDNA

Total RNA or cDNA is incubated with an array of a plurality of pre-immobilized gene specific primers (probes) present electrode surfaces. A different gene specific primer is present on each electrode of the array. The gene specific primers are specific sequencing/extension primers with the 5' or 3' end over the base of interest. The array of primers is hybridized to the RNA of interest in the presence of suitable hybridization buffer. The resultant template/primer nucleic acid duplexes or fragments are then used as substrate in a primer extension reaction by contacting them with reverse-transcriptase/DNA polymerase enzyme and all four deoxynucleotides. When nucleotides are added and extension occurs, the electrostatic response of a group of identical RNA/cDNA molecules creates a unique waveform from which one can identify and evaluate the mass of the molecules for gene expression profiling. See e.g., FIGS. 19A and 19B. O. Modified templates or oligos are immobilized on different surfaces (planar, needle or multi-well plates made by Au, Ti, Pt or any other conductive materials) by using different immobilization techniques such as streptavidin coated paramagnetic beads, primary amino groups, terminal phosphate, mercapto-silane, epoxy silane-derivatised, isothiocyanate, aminophenyl- or aminopropyl-derivatised polylysine and attachment of thio-modified DNA using a heterobifunctional cross-linker, direct deposition of avidin and etc; which are all protocols known to those of skill in the art.

Pre-synthesized gene specific primers (probe) are immobilized onto the electrodes by using above mentioned different immobilization techniques.

The extracted total RNA, PCR products, cDNA or genomics DNA is incubated with oligos for hybridization in the presence of 20 mM Tris-HCl (pH 7.5), 8 mM MgCl$_2$ or any other hybridization buffer. The hybridized template/primer fragments are then used as substrate in a primer extension reaction with presence of reverse transcriptase enzyme or DNA polymerase depending on usage of DNA or RNA and specific dNTPs. When nucleotides are added and extension occurs, the electrostatic response of a group of identical DNA/RNA molecules creates a unique waveform from which one can identify the pattern for use in characterization according to the subject invention.

The above results and discussion demonstrate that a valuable new way to characterize molecular entities in sample is provided. The basic inventive method of the subject invention finds use in a variety of diverse applications, including the detection/characterization of template dependent primer extension reactions and analyte detection applications. Advantages provided by the subject invention include high speed, simple instrumentation and low cost, as well as ready adaptability to high throughput formats. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of detecting an analyte through the occurrence of a polymerase mediated template dependent complementary primer extension reaction in a conducting medium, said method comprising:
    (a) providing a system comprising an immobilized template nucleic acid and a sample;
    (b) forming a template primer duplex nucleic acid made up of template and any complementary primer nucleic acids in the analyte in said sample in contact with said medium, wherein said medium comprises a polymerase and a plurality of nucleotides added to a second electrode in said medium;
    (c) detecting a transient electrical signal indicative of whether or not a primer extension reaction occurs in the medium and produced in said medium by movement of charged nucleotides through the medium towards the immobilized template primer duplex and resultant covalent bonding of said at least one nucleotide to a terminus of said primer nucleic acid; and
    (d) relating said detected transient electrical signal to the occurrence of a polymerase mediated template dependent primer extension reaction in said medium, said transient electrical signal being a signal dependent on complementary primer nucleic acids in the analyte.

2. The method according to claim 1, wherein said medium is an aqueous fluid medium.

3. The method according to claim 1, wherein said medium comprises only one type of nucleotide.

4. The method according to claim 1, wherein said medium comprises at least two different types of nucleotides.

5. The method according to claim 4, wherein said medium comprises dATP, dGTP, dCTP and dTTP.

6. The method according to claim 1, wherein said nucleic acid analyte comprises a SNP (single nucleotide polymorphism) site.

7. The method according to claim 1, wherein said nucleic acid analyte is a nucleic acid from a pathogenic organism.

8. The method according to claim 1, wherein said method is a method of gene expression profiling.

9. The method according to claim 1, wherein said method is a method of monitoring a PCR reaction as the reaction progresses.

10. A method of sequencing a nucleic acid, said method comprising:
    (a) providing a system comprising an immobilized template primer duplex nucleic acid made up of said nucleic acid hybridized to a primer nucleic acid, wherein said immobilized template primer duplex nucleic acid is immobilized on a surface of a working electrode and is in contact with a conducting medium comprising a polymerase;
    (b) adding a plurality of molecules of only one type of nucleotide, at a time to the medium between the working electrode and a second electrode;
    (c) detecting a transient electrical signal produced in said medium by movement of the molecules of one type of nucleotide and covalent bonding if said one type of nucleotide is complementary to a nucleotide at a terminus of said template nucleic acid; and
    (d) determining said sequence of said nucleic acid using said detected transient electrical signal occurring upon movement and binding of a complementary charged nucleotide, said method further comprising the step of: two or more iterations of (a) through (c) to produce a plurality of transient electrical signals from which said sequence of said nucleic acid is determined.

11. The method according to claim 10, wherein said medium alternatively comprises one of dGTP, dATP, dCTP and dTTP and said determining step comprises reading said sequence from a single detected transient electrical signal.

12. The method of claim 1 wherein the medium is in a defined volume between about 10 µl and 0.05 ml.

13. The method of claim 1 further comprising amplifying the transient electrical signal with a differential amplifier having inputs from the two electrodes.

14. The method of claim 1 wherein said step of providing a system further comprises providing multiple immobilized primers, each having a separate electrode.

15. The method of claim 10 wherein the medium is in a defined volume between about 10 µl and 0.05 ml.

16. The method of claim 10 further comprising amplifying the transient electrical signal with a differential amplifier having inputs from the two electrodes.

* * * * *

UNITED STATES PATENT AND TRADEMARK OFFICE
CERTIFICATE OF CORRECTION

| | | |
|---|---|---|
| PATENT NO. | : 7,223,540 B2 | |
| APPLICATION NO. | : 10/345653 | |
| DATED | : May 29, 2007 | |
| INVENTOR(S) | : Pourman et al. | |

It is certified that error appears in the above-identified patent and that said Letters Patent is hereby corrected as shown below:

Column 1:

Insert at line 17:

-- FEDERALLY-SPONSORED RESEARCH OR DEVELOPMENT
This invention was made with Government support under contract HG000205 awarded by the National Institutes of Health. The Government has certain rights in this invention. --

Signed and Sealed this
First Day of January, 2013

David J. Kappos
*Director of the United States Patent and Trademark Office*